US012662698B2

(12) United States Patent
Marggraf-Rogalla et al.

(10) Patent No.: US 12,662,698 B2
(45) Date of Patent: Jun. 23, 2026

(54) COMPOSITION AND METHODS FOR HYBRIDIZATION

(71) Applicant: 42 Life Sciences GmbH & Co. KG, Bremerhaven (DE)

(72) Inventors: Piere Marggraf-Rogalla, Stuhr (DE); Sven Hauke, Bremen (DE)

(73) Assignee: 42 Life Sciences GmbH & Co. KG, Bremerhaven (DE)

( * ) Notice: Subject to any disclaimer, the term of this patent is extended or adjusted under 35 U.S.C. 154(b) by 215 days.

(21) Appl. No.: 15/752,505

(22) PCT Filed: Aug. 19, 2016

(86) PCT No.: PCT/EP2016/069681
§ 371 (c)(1),
(2) Date: Feb. 13, 2018

(87) PCT Pub. No.: WO2017/032702
PCT Pub. Date: Mar. 2, 2017

(65) Prior Publication Data
US 2018/0237840 A1 Aug. 23, 2018

(30) Foreign Application Priority Data

| Aug. 21, 2015 | (EP) | ..................................... | 15002487 |
| Sep. 3, 2015 | (EP) | ..................................... | 15183642 |
| Sep. 7, 2015 | (EP) | ..................................... | 15184010 |
| Sep. 9, 2015 | (EP) | ..................................... | 15184389 |

(51) Int. Cl.
*C12Q 1/6832* (2018.01)
*C12Q 1/6841* (2018.01)

(52) U.S. Cl.
CPC ......... *C12Q 1/6832* (2013.01); *C12Q 1/6841* (2013.01); *C12Q 2527/125* (2013.01); *C12Q 2527/137* (2013.01)

(58) Field of Classification Search
None
See application file for complete search history.

(56) References Cited

U.S. PATENT DOCUMENTS

| 5,376,529 | A | * | 12/1994 | Van Ness | .............. | C12Q 1/6832 |
| | | | | | | 435/6.12 |
| 5,403,711 | A | | 4/1995 | Walder et al. | | |
| 5,420,025 | A | * | 5/1995 | Takagi | ................. | A23C 9/1216 |
| | | | | | | 435/252.35 |
| 6,143,495 | A | | 11/2000 | Lizardi et al. | | |
| 9,108,932 | B2 | * | 8/2015 | Ross, Jr. | .............. | C07D 249/08 |
| 9,109,123 | B2 | * | 8/2015 | Breyer | ..................... | C08K 5/21 |
| 2001/0007032 | A1 | * | 7/2001 | Agyin | .................. | C07D 285/08 |
| | | | | | | 548/128 |
| 2002/0037551 | A1 | * | 3/2002 | Sheppard | ........... | C07K 14/7056 |
| | | | | | | 435/7.1 |

| 2002/0102554 | A1 | | 8/2002 | Utermohlen et al. | | |
| 2003/0166066 | A1 | | 9/2003 | Bard et al. | | |
| 2004/0109843 | A1 | * | 6/2004 | Morishita | ............... | A61P 19/00 |
| | | | | | | 424/85.1 |
| 2005/0090520 | A1 | | 4/2005 | Lindquist | | |
| 2007/0099192 | A1 | * | 5/2007 | Wang | ................... | C12Q 1/6837 |
| | | | | | | 435/6.14 |
| 2008/0089866 | A1 | | 4/2008 | Boden et al. | | |
| 2010/0248231 | A1 | | 9/2010 | Wei et al. | | |
| 2011/0092380 | A1 | | 4/2011 | Stahler et al. | | |
| 2011/0117554 | A1 | | 5/2011 | Benner et al. | | |
| 2011/0229975 | A1 | * | 9/2011 | Matthiesen | .......... | C12Q 1/6832 |
| | | | | | | 536/25.3 |
| 2012/0309951 | A1 | | 12/2012 | Utermohlen et al. | | |
| 2013/0022711 | A1 | * | 1/2013 | Ichihara | .................. | A23L 7/109 |
| | | | | | | 426/549 |
| 2013/0040294 | A1 | * | 2/2013 | Matthiesen | .......... | C12Q 1/6832 |
| | | | | | | 436/501 |
| 2014/0120535 | A1 | * | 5/2014 | Aurich-Costa | ...... | C12Q 1/6841 |
| | | | | | | 435/6.11 |
| 2014/0242589 | A1 | * | 8/2014 | Matthiesen | .......... | C12Q 1/6832 |
| | | | | | | 435/6.11 |
| 2016/0235856 | A1 | | 8/2016 | Montefeltro et al. | | |

FOREIGN PATENT DOCUMENTS

| EP | 2636756 | 9/2013 |
| JP | 2012-518430 | 8/2012 |
| WO | 9402639 | 2/1994 |

(Continued)

OTHER PUBLICATIONS

"Protic solvent", Wikipedia.com, accessed Jun. 29, 2022. (Year: 2022).*
"Ethylene carbonate", Wikipedia.com, accessed Jun. 29, 2022. (Year: 2022).*
"2-Piperidinone", Wikipedia.com, accessed Jun. 29, 2022. (Year: 2022).*
"2-Pyrrolidone", Wikipedia.com, accessed Jun. 29, 2022. (Year: 2022).*
"gamma-Butyrolactone", Wikipedia.com, accessed Jun. 29, 2022. (Year: 2022).*
"Sulfolene", Wikipedia.com, accessed Jun. 29, 2022. (Year: 2022).*
"Researchers Fully Sequence the Y Chromosome for the First Time", National Institute of Standards and Technology, Aug. 23, 2023, pp. 1-4. (Year: 2023).*
"Mammal", Wikipedia.com, accessed May 11, 2023; pp. 1-49. (Year: 2023).*
"How many Species of Bacteria Are There?", wiseGEEK.com; accessed Sep. 23, 2011. (Year: 2011).*

(Continued)

*Primary Examiner* — Bradley L. Sisson
(74) *Attorney, Agent, or Firm* — Hovey Williams LLP; Crissa A. Cook

(57) ABSTRACT
The present invention relates to a composition for use in hybridization, the composition comprising: (a) at least one hybridization probe ("component (a)"); (b) at least one polar protic or polar aprotic solvent ("component (b)") having a cyclic molecule structure; and (c) at least one carboxylic acid amide and/or salts thereof ("component (c)"), in an amount of more than 10 vol %, based on the composition. The invention furthermore relates to a use of this composition, and to methods for detecting nucleic acids and/or chromosomal aberrations in a biological sample by way of hybridization, using the composition.

8 Claims, 4 Drawing Sheets

(56)                    References Cited

FOREIGN PATENT DOCUMENTS

| WO | 02088396 | 11/2002 | | |
| WO | 2010097655 | 9/2010 | | |
| WO | 2010097707 | 9/2010 | | |
| WO | 2011067678 | 6/2011 | | |
| WO | 2013046033 | 4/2013 | | |
| WO | 2013057310 | 4/2013 | | |
| WO | WO-2013057310 A2 * | 4/2013 | .......... | C12Q 1/6832 |
| WO | 2016125091 | 8/2016 | | |

OTHER PUBLICATIONS

"Researchers Fully Sequence the Y Chromosome for the First Time", National Institute of Standards and Technology, Aug. 23, 2023 (Year: 2023).*

International Search Report and Written Opinion in corresponding PCT Application Serial No. PCT/EP2016/069681, mailed Dec. 13, 2016 (English translation attached).

Matthiesen, et al., "Fast and Non-Toxic In Situ Hybridization without Blocking of Repetitive Sequences", PLoS One, Jul. 2012, vol. 7, issue 7, 8 pages.

Pajor, et al., "State-of-the-Art FISHing: Automated Analysis of Cytogenetic Aberrations in Interphase Nuclei", Cytometry Part A, 2012 volume 81A, issue 8, pp. 649-663.

Van Der Logt, et al., "Fully Automated Fluorescent in situ Hybridization (FISH) Staining and Digital Analysis of HER2 in Breast Cancer: A Validation Study", PLoS One, Apr. 6, 2015, vol. 10, issue 4, pp. 1-12.

Declaration of Dr. Jens Mollerup, dated May 11, 2020.

Curriculum Vitae of Dr. Jens Mollerup, dated May 11, 2020.

Histology FISH Accessory Kit, Code K5799, Instructions for use, dated Jan. 2020.

Opposition to corresponding European Patent Application Serial No. 3133166, dated May 13, 2020.

CAS registry No. 9002-93-1, Apr. 2021, "Polyethylene glycol mono(4-tert-octylphenyl) ether", retrieved from https:// commonchemistry.cas.oro/detail?ref=9002-93-1.

Wikipedia, "Triton X-100", retrieved from https://en.wiqedia.org(w/ indexpp?title=Triton X-100&oldid=1011676555, dated Mar. 12, 2021.

CAS registry No. 9005-64-5, Apr. 2021, "Polyoxyethylene sorbitan monolaurate", retrieved from https://commonchemistry.cas.orq/ detail?ref=9005-64-5.

Wikipedia, "Polysorbate 20", retrieved from https://en.wikipedia. org/w/index.php?title=Polysorbate_20&oldid=1007307385, Feb. 17, 2021.

Opposition to corresponding European Patent Application Serial No. 3133166, dated Apr. 12, 2021.

Wikipedia, "Polyalkylenglycolether", 2021, retrieved from https:// de.wikipedia.org/w/index.php?title=Polyalkylenglycolether&oldid= 212365468.

Opposition in corresponding European Patent Application Serial No. 3133166, dated Dec. 23, 2021.

Declaration by Kenneth Petersen, dated.

Curriculum Vitae for Kenneth Petersen.

Statement of Dr. Piere Marggraf-Rogalla.

Curriculum Vitae for Dr. Piere Marggraf-Rogalla.

Excerpt of textbook "Organic Chemistry", 1980, 4 pages.

Wikipedia, "Polyalkylene glycol ether" retrieved from: https://de. wikipedia.org/w/index.php?title=Polyalkylenglycolether&oldid= 23702040; dated Nov. 12, 2006.

Wikipedia, "Polyalkylene glycol ether" retrieved from: https://de. wikipedia.org/w/index.php?title=Polyalkylenglycolether&oldid= 138979669, dated Feb. 18, 2015.

Opposition to corresponding European Patent Application Serial No. 3133166, dated Mar. 1, 2022.

Final Office Action in co-pending U.S. Appl. No. 18/497,290, dated Apr. 7, 2025.

"Viruses", Wikipedia.com, accessed Sep. 8, 2023.

"Fungi," Wikipedia.com; accessed Sep. 8, 2023.

"Insect", Wikipedia.com; accessed Sep. 10, 2020.

"Plant," Wikipedia.com; accessed Sep. 8, 2023.

"Murinae," Wikipedia.com, accessed Jun. 10, 2024.

"Fish," Wikipedia.com, accessed Sep. 8, 2023.

"Archaea," Wikipedia.com, accessed Sep. 8, 2023.

"Algae," Wikipedia.com, accessed Mar. 4, 2016.

"Protozoa," Wikipedia.com, accessed May 11, 2016.

* cited by examiner

I.)
Hybridization compositions comprising formamide, CPAL and dextran sulfate after 16 hours II.)
Hybridization compositions comprising formamide, CPAL and dextran sulfate after 2 hours III.)
Hybridization compositions comprising formamide and CPAL, but no dextran sulfate, after 2 hours a) Normal cells b) HER2 break result (e.g., amplification)

🟠 = orange
⚫ = green

COMPOSITION AND METHODS FOR HYBRIDIZATION

RELATED APPLICATIONS

This application is the U.S. National Stage of International Patent Application No. PCT/EP2016/069681, filed Aug. 19, 2016, which is hereby incorporated by reference in its entirety, and which claims priority to European Patent Application No. 15002487.5, filed Aug. 21, 2015, European Patent Application No. 15183642.6, filed Sep. 3, 2015, European Patent Application No. 15184010.5, filed Sep. 7, 2015 and European Patent Application No. 15184389.3, filed Sep. 9, 2015.

BACKGROUND

The present invention is directed to the technical field of detection methods for nucleic acids, in particular DNA and/or RNA.

In particular, the present invention relates to a composition for use in hybridization, and in particular for the identification and/or for the detection of nucleic acids, and to the use thereof according to the invention. Furthermore, the present invention relates to a method for detecting nucleic acids or of chromosomal aberrations. Finally, the present invention relates to a kit for detecting nucleic acids or chromosomal aberrations.

Many tumor diseases are based on structural and numerical chromosome mutations, such as translocations, inversions, segmental duplications, deletions, insertions, duplications, aneuploidies and amplifications. These changes are generally detected as predictive, prognostic or differential diagnostic markers by way of in situ hybridization (ISH).

In situ hybridization is based on the hybridization or pairing of complementary bases of single nucleic acid strands, and in particular single DNA strands, so that specific nucleic acid sequences can be detected in a sample, and in particular in a tissue or a cell preparation. For this purpose, directly or indirectly labeled, synthetically produced probes are hybridized with single nucleic acid strands of the sample and subsequently detected.

For detection purposes, fluorescent-labeled nucleic acid fragments or fluorescent-labeled hybridization probes (fluorescence ISH (FISH)) may be used, among other things. Moreover, it is possible to use antigen-labeled probes, and in particular hapten-labeled probes, which are subsequently visualized using antibodies by way of color reactions, thereby allowing analysis by way of light microscopy (bright field ISH (BrISH), chromogenic ISH (CISH), silver-enhanced ISH (SISH)).

To carry out in situ hybridizations, usually first a biological sample to be examined, and in particular a preparation, preferably based on tissue sections or cytological preparations, is provided. For preparation for the in situ hybridization, the samples are immobilized on glass slides and dehydrated. To allow the labeled probes to hybridize to the nucleic acids, and in particular the RNA or DNA, in the cells or nuclei, first a denaturing step is carried out, so that the nucleic acid to be detected, or the nucleic acid segment to be detected, and furthermore the hybridization probes used, are present in single-stranded form in the sample. It is possible to denature the sample and the hybridization probe separately from one another, or jointly within the meaning of co-denaturing. Thereafter, the hybridization probes used are hybridized to the nucleic acids comprised in the sample. The hybridization probes are usually comprised in dissolved or stabilized form in hybridization solutions, which are applied to the samples to be examined for hybridization. The hybridized hybridization probes, or hybridization probes annealed to the target nucleic acids, can finally be detected as was already described above.

As will be described hereafter in detail, the hybridization conditions influencing the specificity of binding of the hybridization probes and the stringency of the hybridization process play a decisive role in obtaining results that can be evaluated well:

For the hybridization process, or the success of the hybridization process, in particular the denaturing of the sample and of the hybridization probes, and subsequent renaturing of the nucleic acids, and in particular of the DNA, which is to say the hybridization of single nucleic acid strands in the sample with single nucleic acid strands of the hybridization probes, are of central importance.

The separation of double-stranded nucleic acid molecules into single-stranded nucleic acids, or denaturing, may, in particular, take place at high temperatures of approximately 90 to 100° C. However, temperatures this high are harmful to the morphology of the biological sample, and in particular of the preferably used tissue sections or cells.

So as to preserve the morphology of the samples, and additionally improve the stringency of the hybridization, in situ hybridization in the prior art is usually carried out using formamide-containing solutions so as to denature the double-stranded nucleic acids in the biological samples. By using formamide in the solutions utilized for the hybridization, the melting temperature of double-stranded nucleic acids, and in particular of DNA-DNA and DNA-RNA duplexes, which generally ranges between 9° and 100° C., is lowered to 65 to 80° C.

Some of the hybridization solutions known from the prior art, however, are associated with certain shortcomings, as will be described hereafter:

While the use of formamide-containing hybridization solutions allows the morphology of the samples used, and thus also the hybridization result, to be improved due to the lower melting point of the DNA, formamide-containing hybridization solutions are usually associated with very long reaction durations. The reason is that formamide significantly slows down the renaturing process, which is to say the annealing or binding of the hybridization probes on the one hand, and the nucleic acids that are comprised in the samples being examined and that are to be detected on the other hand. The prior art usually provides for hybridization or renaturing durations of 10 to 24 hours. In isolated instances, a hybridization or renaturing duration of up to 72 hours may even be necessary.

To overcome the problem of long hybridization durations, approaches are known from the prior art which provide a replacement of formamide in the hybridization solutions with other solvents. WO 91/02088 A1, for example, uses lactam-based solvents in hybridization solutions. WO 00/69899 A1 describes compositions for stabilizing nucleic acids or nucleic acid analogs for biotechnology applications which contain solvents different from formamide for dissolving nucleic acids. Frequently, however, the signal patterns achieved with these formamide-free solutions are not satisfactory or difficult to evaluate.

Moreover, the hybridization solutions known so far from the prior art, which contain the locus-specific hybridization probes necessary for in situ hybridizations, have additional disadvantages, as will be described hereafter:

Often, the signals yielded by known hybridization solutions are not strong when carrying out in situ hybridizations as rapid tests, during which signal patterns that can be evaluated well are generated even when using short hybridization durations, even though a need exists in this regard, for example for carrying out rapid tests for prenatal or post-natal diagnostics or for tumor cytogenetics.

Moreover, the hybridization solutions known from the prior art are not very suitable, or suitable only to a very limited extent, for use in automated in situ hybridization processes. Compared to non-automatic or manually conducted in situ hybridization processes, larger amounts or volumes of hybridization solutions must be applied to the samples with automated methods. Using the hybridization solutions known from the prior art, it has not been possible so far to also dissolve or to stabilize the amounts of hybridization probes required for in situ hybridization in high-volume solutions, or in highly diluted form, in such a way that good hybridization results can be achieved. However, since hybridization probes are very costly, so far, no approach is known, or no hybridization compositions are known, from the prior art for automated in situ hybridizations which can also be carried out taking economic aspects into consideration.

It is thus the object of the present invention to provide compositions that are suitable for use in in situ hybridization, and in particular for detecting nucleic acids in a biological sample, and that at least substantially avoid, or at least mitigate, the above-described disadvantages of the prior art.

In particular, it is the object of the present invention to provide compositions or hybridization solutions for in situ hybridization which are also suitable for use in automated in situ hybridization which are also suitable for use in automated in situ hybridization processes and/or allow automated in situ hybridization processes to be carried out cost-effectively. Furthermore, it is the object of the present invention to provide compositions for in situ hybridization which yield good results, or result in signal patterns that can be evaluated well, both with short and with long hybridization or renaturing durations.

DESCRIPTION

To achieve the above-described object, the present invention proposes a composition according to claim 1; further advantageous embodiments are the subject matter of the relevant dependent claims.

The present invention furthermore relates to the use of a composition in accordance with the present invention according to the relevant independent claim.

The present invention additionally relates to a method for detecting nucleic acids or chromosomal aberrations according to the relevant independent claim.

Finally, the present invention relates to a kit or kit of parts or system for detecting nucleic acids or chromosomal aberrations according to the relevant independent claim; further advantageous properties are the subject matter of the relevant independent claim.

It goes without saying that hereafter specific configurations, embodiments or the like, which are only described in connection with one aspect of the invention, also apply accordingly with respect to the other aspects of the invention, without this requiring express mention.

Furthermore, it should be noted with respect to all relative or percentage-based, and in particular weight-based or volume-based, quantity information mentioned hereafter that these quantities are to be selected by a person skilled in the art within the scope of the present invention in such a way that the respective ingredients, active agents, additives or auxiliary agents or the like in sum always result in 100% of 100 wt. %. This, however, goes without saying for a person skilled in the art.

Additionally, a person skilled in the art may deviate from the figures, ranges or quantities described hereafter, either based on the application or as necessitated by the individual situation, without departing from the scope of the present invention.

Additionally, all parameter information or the like described hereafter can essentially be determined or ascertained by way of standardized or explicitly described determination procedures, or by way of determination methods commonly used by a person skilled in the art.

Thus—according to a first aspect according to the invention—the present invention relates to a composition, and in particular a composition for use in hybridization, in particular in situ hybridization, preferably automated in situ hybridization, in particular for the identification and/or for the detection of nucleic acids, preferably RNA and/or DNA, in a biological sample, preferably in one or more cells and/or in one or more nuclei, the composition comprising:

(a) least one hybridization probe ("component (a)");
(b) at least one polar protic or polar aprotic solvent ("component (b)"), preferably having a cyclic molecule structure; and
(c) at least one carboxylic acid amide and/or salts thereof ("component (c)"), in particular formamide and/or salts thereof, in an amount of more than 10 vol %, based on the composition.

In other words, it is thus provided according to the invention to provide compositions for hybridization, synonymously also referred to as hybridization solutions, in which the hybridization probes, based on the combination of at least one deliberately selected polar protic or polar aprotic solvent and at least one carboxylic acid amide or salts thereof, preferably formamide, are comprised in stabilized or dissolved form in an amount of more than 10 wt. %, based on the composition.

Within the scope of the present invention, it was found, as a complete surprise, that the deliberate combination of at least one specifically selected polar protic or polar aprotic solvent on the one hand, and at least one carboxylic acid amide or salts thereof, in particular formamide or salts thereof, on the other hand, each in defined amounts, allows even small amounts of hybridization probes, which is to say highly diluted hybridization probes, to be stabilized in high-volume hybridization solutions. By way of these high-volume hybridization solutions according to the invention comprising the hybridization probes in highly diluted form, surprisingly, excellent signal patterns are also achieved within the scope of automated in situ hybridization methods. So far, this has not been successful in the prior art.

Furthermore, it came as a complete surprise that the hybridization solutions according to the invention are not only suitable for use in automated hybridization processes, but additionally lead to excellent results or signal patterns both with short and with long hybridization or renaturing durations. The hybridization solutions according to the invention are thus also suitable for use in rapid tests, such as rapid ISH or rapid FISH, or so-called "flexible" in situ hybridizations having variable hybridization times.

The present invention, overall, is associated with numerous advantages and special characteristics which are discussed hereafter in a non-limiting manner and shall be considered an indication of the patentability of the present invention.

As described above, it was surprisingly possible within the scope of the present invention to stabilize even small amounts of hybridization probes in high-volume hybridization solutions or compositions, so that automatic or automated in situ hybridization processes may now also be carried out yielding signal patterns that can be evaluated well and have strong signals, without having to use larger probe amounts compared to manual or established hybridization processes.

The compositions or hybridization solutions according to the invention are thus in particular advantageous with respect to economic aspects of the hybridization processes since it is now possible to carry out the automated hybridization processes in a cost-efficient manner. Moreover, the efficiency of in situ hybridization processes as a whole is increased since automated processes are associated with a higher sample throughput.

Furthermore, the hybridization solutions according to the invention are versatile in their use since they are suitable for different in situ hybridization processes. In particular, the compositions according to the invention can be used for fluorescence in situ hybridizations (FISH), bright field in situ hybridizations (BrISH), chromogenic in situ hybridizations (CISH) and/or silver-enhanced in situ hybridizations (SISH) alike.

Moreover, the compositions are also suitable for in situ hybridizations having long and short hybridization or renaturing durations. In particular within the scope of rapid tests having short hybridization durations, such as rapid ISH methods, or flexible in situ hybridizations having variable hybridizations duration, the compositions according to the invention yield excellent results. This is surprising, in particular against the background that the compositions according to the invention comprise formamide in amounts of at least 10 wt. %, and formamide usually requires long hybridization times. The short hybridization times, despite the use of formamide, are only made possible by the deliberate combination according to the invention of the at least one carboxylic acid amide, in particular the formamide, with at least one polar protic or polar aprotic solvent in respective defined amounts.

The compositions according to the invention, overall, are characterized by the excellent stability thereof, and in particular of the hybridization probes contained therein. The stability of the compositions may be increased even further when the compositions contain stabilizing or blocking agents, in particular those based on nucleic acids and/or nucleic acid analogs, since these prevent premature degradation of the hybridization probes. Surprisingly, the combination according to the invention of at least one polar protic or polar aprotic solvent and formamide allows large amounts of stabilizing or blocking agents, in particular those based on nucleic acids, to be dissolved in the compositions according to the invention.

Finally, the signal patterns of the in situ hybridizations obtained by way of the compositions according to the invention overall stand out with the excellent quality thereof. Distinct signals that can be evaluated well are generated. Moreover, it is also possible to at least substantially minimize non-specific signals or non-specific background staining, which is to say the hybridization compositions according to the invention are characterized by the excellent stringency thereof.

To provide a better understanding of the present invention, central terms and designations of the composition according to the invention are defined hereafter:

The in situ hybridization used according to the invention is based on the hybridization or pairing of complementary bases of single nucleic acid strands, and in particular single DNA strands, so that specific nucleic acid sequences, which is to say the chromosome or DNA portions to be detected, can be detected in a sample, such as a tissue or a cell preparation. Within the scope of the in situ hybridization, directly or indirectly labeled, synthetically produced, and in particular locus-specific, hybridization probes based on nucleic acids are hybridized to single nucleic acid strands of the sample and subsequently detected.

In principle, the in situ hybridization may take place or be carried out at various stages of the cycle of the cells or nuclei being examined, wherein it has become established procedure to carry this out during metaphase, when the chromosomes are comprised in a condensed state, or during interphase, when the chromosomes are comprised in decondensed form. Depending on the goal or purpose of the in situ hybridization, it is not always possible to carry out the process on condensed chromosomes during metaphase, in particular, for example, when examining the cells of solid tumors for chromosomal aberrations. In these cases, the in situ hybridization is carried out on cells in the interphase.

The hybridization probes are preferably locus-specific. Within the scope of the present invention, locus-specific hybridization probes shall be understood to mean probes that are specific for a chromosome portion or DNA portion to be detected, or probes complementary to a chromosome portion or DNA portion to be detected of the DNA material or the genetic material, in a sample to be examined. It may also be provided to detect the RNA of preferably individual genes or to use locus-specific hybridization probes, which are specific for the RNA of preferably individual genes. Usually, the hybridization probes used according to the invention are based on nucleic acids or nucleic acid fragments and/or nucleic acid analogs, and they are capable of specifically binding or hybridizing to the chromosome portion or DNA portion to be detected. The nucleic acids and/or nucleic acid analogs may, in particular, be DNA, RNA, locked nucleic acids (LNA) or peptide nucleic acids (PNA). For detection purposes, the locus-specific hybridization probes are moreover directly or indirectly labeled with detection labels. The chromosome portion or DNA portion to be detected may have a variable length. In particular, it may be provided that a chromosome portion or DNA portion to be detected, or RNA to be detected, partially or completely comprises a single or an individual gene. Likewise, it may be provided that a chromosome portion or DNA portion to be detected partially or completely comprises multiple genes, especially neighboring genes, and preferably two genes. Furthermore, it may be provided within the scope of the present invention that the hybridization probes used are whole chromosome painting (WCP) hybridization probes or partial chromosome painting (PCP) probes, which comprise a plurality of different locus-specific hybridization probes, which are each labeled with at least one detection label and allow entire chromosomes and/or chromosome sections to be detected. As far as the configuration of the hybridization probes per se is concerned, a person skilled in the art will be familiar with such configurations, so that no additional information is required in this regard.

As far as additionally the term 'biological sample' is concerned, this may in particular be tissue or tissue components to be examined, and in particular tissue sections. Moreover, however, it may also be provided to use individual cells or cell aggregations or isolated nuclei as biological samples.

Within the scope of the present invention, polar aprotic solvents shall be understood to mean in particular non-aqueous solvents, which contain no ionizable proton in the molecule. In other words, aprotic solvents are in particular based on molecules that do not comprise any functional groups from which hydrogen atoms may be given off or dissociate in the form of protons. Moreover, within the scope of the present invention, aprotic polar solvents are preferably substituted with highly polarizing functional groups, such as carbonyl groups, nitrile groups or thiol groups, so that the underlying molecules of the solvent have dipole moments. Polar aprotic solvents can be present both in aliphatic form and in aromatic or cyclic form. According to the invention, it has proven to be particularly advantageous to use polar aprotic solvents having a cyclic molecule structure. Moreover, it is provided within the scope of the present invention that the compositions according to the invention do not contain any dimethyl sulfoxide (DMSO) or are free of DMSO. For more in-depth details regarding the definition of polar aprotic solvent, reference may be made to RÖMPP Chemielexikon, 10th edition, Thieme Verlag, Stuttgart New York, 1996, page 241, keyword: "Aprotische Lösungsmittel (Aprotic solvents)" and the literature referenced therein, which is hereby included fully by reference.

In contrast, within the scope of the present invention, polar protic solvents shall be understood to mean in particular non-aqueous solvents which comprise an ionizable protein in the molecule and/or are capable of donating an ionizable protein and/or which are capable of forming hydrogen bonds. In other words, within the scope of the present invention, polar protic solvents are in particular based on molecules that include functional groups from which hydrogen atoms can be given off or dissociate in the form of protons, or which are functionalized in such a way that hydrogen atoms can be given off or dissociate in the form of protons. Polar protic solvents may also be referred to as polar amphiprotic solvents. For more in-depth details regarding the definition of polar protic solvent, reference may be made to RÖMPP Chemielexikon, 10th edition, Thieme Verlag, Stuttgart New York, 1996, page 3597, keyword: "Protische Lösungsmittel (Protic solvents)" and the literature referenced therein, which is hereby included fully by reference.

Within the scope of the present invention, carboxylic acid amides shall be understood to mean derivatives of ammonia and of primary and secondary amines, in which one or more hydrogen atoms of the nitrogen are replaced with carboxylic acid moieties or substituted by carboxylic acid moieties. Particularly good results with respect to the in situ hybridizations are achieved when the compositions according to the invention comprise formamide as the carboxylic acid amide, which is the amide derived from formic acid and thus the simplest carboxylic acid amide. In a particularly preferred embodiment, the carboxylic acid amide is thus formamide. As far as additionally the amount used of carboxylic acid amide, and in particular of formamide, is concerned, according to the invention this amount is more than 10 vol %, which is to say an amount of exactly 10 vol % is excluded.

The composition according to the invention can be configured in a variety of ways. Preferred embodiments are described hereafter in detail.

Within the scope of the present invention, surprisingly it was possible to obtain signal patterns that can be evaluated well within the scope of in situ hybridizations, even when using high-volume hybridization compositions containing the hybridization probes only in small concentrations and/or amounts, or containing small amounts of hybridization probes, based on the volume used.

Particularly good results are achieved according to the invention when composition (a) comprises the at least one, preferably locus-specific, hybridization probe in a concentration in the range of 0.1 ng/μl to 50 ng/μl, in particular 0.5 ng/μl to 50 ng/μl, especially 0.7 ng/μl to 8 ng/μl, and preferably 1 ng/μl to 5 ng/μl, based on the composition. Within the scope of the present invention, it came as a complete surprise that the, preferably locus-specific, hybridization probes can be stabilized in the aforementioned concentrations in the hybridization solutions according to the invention, and thus result in excellent signal patterns even when used in automated hybridization processes. So far, it has not been successful in the prior art to provide hybridization solutions that also allow automated hybridization processes to be carried economically or cost-effectively. As far as specifically the at least one polar protic or polar aprotic solvent, preferably having a cyclic molecule structure, is concerned, this is preferably selected from the group consisting of solvents having lactone, sulfone, nitrile, carbonate and/or amide functionality, and more preferably from the group consisting of solvents having lactone, sulfone, carbonate and/or amide functionality. The term "functionality" in the present context describes the presence of functional groups in a molecule. In other words, the polar protic or polar aprotic solvent is preferably selected from the group consisting of solvents having at least one functional lactone, sulfone, nitrile, carbonate and/or amide group.

In particular, it may be provided that the at least one polar aprotic or polar protic solvent is selected from the group consisting of ethylene carbonate, pyrrolidones, lactams, ethylene sulfite, γ-butyrolactone, ethylene trithiocarbonate, propylene carbonate and/or sulfolane, particularly preferably ethylene carbonate and/or pyrrolidones, and more preferably ethylene carbonate.

It may also be provided within the scope of the present invention that the at least one solvent, preferably having a cyclic molecule structure, is a polar aprotic solvent, in particular selected from cyclic carbonates (cyclic carbonate esters), in particular cyclic carbonate esters of alkylene glycols, preferably ethylene carbonate (1,3-dioxolan-2-one) and propylene carbonate, and particularly preferably ethylene carbonate, and cyclic monothiocarbonates, dithiocarbonates and trithiocarbonates, and in particular ethylene sulfite and ethylene trithiocarbonate.

Furthermore, good results are achieved according to the invention when the at least one solvent, preferably having a cyclic molecule structure, is a polar aprotic solvent, in particular selected from aprotic cyclic amides (lactams), in particular N-alkyl-substituted pyrrolidones, and preferably n-methyl-2-pyrrolidone and/or N-ethyl-2-pyrrolidone.

It may also be provided according to the invention that the at least one solvent, preferably having a cyclic molecule structure, is a polar protic solvent, in particular selected from protic cyclic amides (lactams), in particular protic cyclic amides (lactams) having a hydrogen atom on the amide nitrogen (lactam nitrogen), preferably selected from the group consisting of 2-pyrrolidone (γ-butyrolactam), 3-pyrrolidone, caprolactams and/or 2-piperidone (valerolactam), particularly preferably pyrrolidones, and most particularly preferably 2-pyrrolidone (γ-butyrolactam).

The at least one polar protic or polar aprotic solvent preferably has a cyclic molecule structure. Preferred cyclic molecule structures are those having a ring system including five or six ring atoms. The cyclic molecule structure may be a homocycle or a heterocycle, and preferably is a heterocycle. A heterocycle is a compound comprising ring-forming atoms of at least two different elements. In addition to ring-forming carbon atoms, the heterocycle preferably also comprises one or more ring-forming nitrogen, sulfur and/or oxygen atoms, and preferably one or more nitrogen atoms (N-heterocycle) and/or one or more oxygen atoms. Furthermore, it may be provided within the scope of the present invention that the at least one solvent is a polar protic solvent having a cyclic molecule structure, wherein the cyclic molecule structure comprises an N-heterocycle having a free hydrogen atom at the nitrogen atom.

The cyclic molecule structure preferably includes lactone, sulfone, nitrile, carbonate and/or amide functionality, and more preferably lactone, sulfone, carbonate and/or amide functionality. In a preferred embodiment, the invention thus relates to a composition comprising or consisting of: (a) at least one hybridization probe ("component (a)"); (b) at least one polar protic or polar aprotic solvent having a cyclic molecule structure, wherein the cyclic molecule structure has lactone, sulfone, carbonate and/or amide functionality ("component (b)"); and at least one carboxylic acid amide and/or salts thereof ("component (c)") in an amount of more than 10 vol %, based on the composition.

According to a particularly preferred embodiment of the present invention, it may be provided that the at least one polar protic or polar aprotic solvent is selected from the group consisting of ethylene carbonate, 2-piperidone (valerolactam), 2-pyrrolidone (γ-butyrolactam), 3-sulfolene ("butadiene sulfone") and/or γ-butyrolactone. The best results are achieved according to the invention when the polar protic or polar aprotic solvent is γ-butyrolactone, 2-pyrrolidone (γ-butyrolactam) and/or ethylene carbonate. In this connection, reference is also made to the exemplary embodiments carried out by the applicant and described below, which demonstrate the superior properties of the above-mentioned polar protic or polar aprotic solvents in the compositions according to the invention.

By using at least one polar protic or polar aprotic solvent in the composition according to the invention—in particular in combination with at least one carboxylic acid amide, preferably formamide—it is possible to compensate for the disadvantages associated with the use of formamide in hybridization solutions, such as long hybridization times. Moreover, without intending to be bound to this theory, the use of polar protic or aprotic solvents in the compositions according to the invention increases the solubility for nucleic acids as a whole, which in turn improves the stability of the hybridization compositions according to the invention. As a result of the good solubility capability for nucleic acids, it is possible to introduce large amounts of non-hybridizing, non-specific nucleic acids, and in particular stabilization DNA, as so-called blocking or stabilizing agents into the compositions, which prevent degradation of the, preferably locus-specific, hybridization probes, and additionally improve the overall signal pattern and prevent signals from non-specific bonds or hybridizations, which is to say increase the stringency.

As far the amount used of the at least one polar protic or polar aprotic solvent is concerned, this may vary within wide ranges. According to the invention, it may in particular be provided that composition (b) comprises the at least one polar protic or polar aprotic solvent, preferably having a cyclic molecule structure, in an amount that does not result in the denaturing of nucleic acids. Within the scope of the present invention, it is in particular provided to dissolve and stabilize the nucleic acids in the composition according to the invention by way of the at least one polar protic or polar aprotic solvent, wherein the solvent, however, is used in an amount that alone, which is to say without the additional use of at least one carboxylic acid amide and/or further denaturing agents, would not result in the denaturing of the nucleic acids.

In particular, the composition according to the present invention can comprise the at least one polar protic or polar aprotic solvent, preferably having a cyclic molecule structure, in an amount in the range of 0.5 to 40 vol % or wt %, in particular 1 to 35 vol % or wt %, especially 2 to 30 vol % or wt %, preferably 5 to 20 vol % or wt %, and particularly preferably 7 to 15 vol % or wt %, based on the composition.

It is furthermore preferred within the scope of the present invention when composition (b) comprises the at least one polar protic or polar aprotic solvent, preferably having a cyclic molecule structure, in an amount of at least 0.5 vol % or wt %, in particular at least 1 vol % or wt %, especially at least 2 vol % or wt %, preferably at least 5 vol % or wt %, particularly preferably at least 7 vol % or wt %, and most particularly preferably at least 10 vol % or wt %. Likewise, it can be provided that composition (b) comprises the at least one polar protic or polar aprotic solvent, preferably having a cyclic molecule structure, in an amount of no more than 50 vol % or wt %, in particular no more than 40 vol % or wt %, especially no more than 30 vol % or wt %, preferably no more than 20 vol % or wt %, particularly preferably no more than 15 vol % or wt %, and most particularly preferably no more than 13 vol % or wt %.

The above percentage information with respect to the at least one polar protic or polar aprotic solvent is preferably information in percent by weight. In other words, the composition according to the present invention preferably comprises the at least one polar protic or polar aprotic solvent, preferably having a cyclic molecule structure, in an amount in the range of 0.5 to 40 wt %, in particular 1 to 35 wt %, especially 2 to 30 wt %, preferably 5 to 20 wt %, and particularly preferably 7 to 15 wt %, based on the composition.

Within the scope of the present invention, it has been shown in the overall that adhering to the aforementioned quantity ranges significantly improves the resulting signal patterns. The amount of the at least one carboxylic acid amide or of salts thereof, in particular of the formamide or salts thereof, has also been found to be a critical factor with respect to the signal strengths and signal patterns. In connection with the amounts of the at least one polar protic or polar aprotic solvent on the one hand, and of the at least one carboxylic acid amide, in particular of the formamide, on the other hand, reference is also made to the exemplary embodiments carried out by the applicant and described in detail hereafter, which demonstrate that only the use of specifically selected amounts of solvents and carboxylic acid amide results in the excellent signal patterns when carrying out in situ hybridizations, in particular in an automated system or as rapid tests having short or flexible hybridization durations.

Within the scope of the present invention, it may in particular be provided that composition (c) comprises the at least one carboxylic acid amide and/or salts thereof, and in particular formamide and/or salts thereof, in an amount that results in the denaturing of nucleic acids. In a preferred embodiment, composition (c) comprises formamide and/or salts thereof in an amount that results in the denaturing of nucleic acids or is suitable for denaturing nucleic acids. In other words, it may thus be provided within the scope of the present invention that the composition comprises the at least one carboxylic acid amide, and in particular formamide, in an amount that alone, which is to say without the use of a polar protic or polar aprotic solvent, would already result in the denaturing of the nucleic acids.

As far as the amounts used of the at least one carboxylic acid amide are concerned, it has proven advantageous for composition (c) to comprise the at least one carboxylic acid amide and/or salts thereof, and in particular formamide and/or salts thereof, in an amount in the range of 10 to 60 vol %, in particular 15 to 50 vol %, especially 17 to 40 vol %, and preferably 20 to 30 vol %, based on the composition. In a preferred embodiment, the composition according to the invention comprises the at least one carboxylic acid amide and/or salts thereof, and in particular formamide and/or salts thereof, in an amount in the range of 17 to 40 vol %. In a still more preferred embodiment, the composition according to the invention comprises the at least one carboxylic acid amide and/or salts thereof, and in particular formamide and/or salts thereof, in an amount in the range of 20 to 30 vol %.

Moreover, it may be provided for composition (c) to comprise the at least one carboxylic acid amide and/or salts thereof, and in particular formamide and/or salts thereof, in an amount of at least 10 vol %, in particular at least 15 vol %, especially at least 17 vol %, and preferably at least 20 vol %, based on the composition. Likewise, it may be provided for composition (c) to comprise the at least one carboxylic acid amide and/or salts thereof, and in particular formamide and/or salts thereof, in an amount of no more than 60 vol %, in particular no more than 50 vol %, especially no more than 40 vol %, and preferably no more than 30 vol %, based on the composition. In a preferred embodiment, the composition according to the invention comprises the at least one carboxylic acid amide and/or salts thereof, and in particular formamide and/or salts thereof, in an amount of at least 17 vol %, based on the composition. In an even more preferred embodiment, the composition according to the invention comprises the at least one carboxylic acid amide and/or salts thereof, and in particular formamide and/or salts thereof, in an amount of at least 20 vol %, based on the composition.

As mentioned above, amounts of the carboxylic acid amide and/or of salts thereof of more than 10% have proven particularly useful. It is thus particularly preferred according to the invention for composition (c) to comprise the at least one carboxylic acid amide and/or salts thereof, and in particular formamide and/or salts thereof, in an amount between 10 and 60 vol %, in particular between 15 and 50 vol %, especially between 17 and 40 vol %, and preferably between 20 and 30 vol %, based on the composition. In a particularly preferred embodiment, composition (c) comprises formamide and/or salts thereof in an amount between 17 and 40 vol %.

Moreover, it is particularly preferred for composition (c) to comprise the at least one carboxylic acid amide and/or salts thereof, and in particular formamide and/or salts thereof, in an amount of more than 10 vol %, in particular more than 15 vol %, especially more than 17 vol %, and preferably more than 20 vol %, based on the composition. In a particularly preferred embodiment, composition (c) comprises formamide and/or salts thereof in an amount of more than 17 vol %.

In one embodiment, the composition according to the invention comprises more than 10 vol % of the carboxylic acid amide and/or salts thereof, and preferably formamide and/or salts thereof. In one more preferred embodiment, the composition according to the invention comprises more than 20 vol % of the carboxylic acid amide and/or salts thereof, and preferably formamide and/or salts thereof. In addition to the absolute amounts used, it has proven to be advantageous with respect to the signal patterns obtained by way of the composition according to the invention if the at least one polar protic or polar aprotic solvent one the one hand, and the at least one carboxylic acid amide, and in particular formamide, on the other hand, are used in a defined quantity ratio with respect to one another.

Particularly good results are achieved within the scope of the in situ hybridizations when the composition comprises component (b) and component (c), or the at least one polar protic or polar aprotic solvent, preferably having a cyclic molecule structure, and the at least one carboxylic acid amide and/or salts thereof, and in particular formamide and/or salts thereof, in a volume-based ratio in the range of 1:100 to 50:1, in particular 1:50 to 20:1, especially 1:25 to 10:1, preferably 1:10 to 5:1, particularly preferably 1:5 to 1:1, and most particularly preferably 1:3 to 1:2.

Additionally, it has proven advantageous when the composition comprises at least one polysaccharide ("component (d)"), in particular biopolysaccharide, especially neutral biopolysaccharide, preferably dextran and/or the derivatives or salts thereof, and particularly preferably dextran sulfate. Within the scope of the present invention, surprisingly it has been found that the hybridization results can be improved yet again by way of the compositions according to the invention when the compositions according to the invention comprise at least one polysaccharide, in particular for stabilization. In this regard, reference is made to the exemplary embodiments according to the invention, which prove the effect of the polysaccharide in the compositions. Particularly good results are achieved when the polysaccharide used is dextran sulfate.

As far as the amount of the at least one polysaccharide in the compositions is concerned, it has proven to be particularly advantageous when the composition comprises component (d) in an amount in the range of 0.1 to 50 wt %, in particular 1 to 40 wt %, especially 5 to 30 wt %, and preferably 10 to 20 wt %, based on the composition. In a preferred embodiment, the composition comprises 5 to 30 wt % of the at least one polysaccharide, and particularly preferably 5 to 30 wt % dextran sulfate.

Moreover, it may be provided within the scope of the present invention that the composition comprises at least one chemical buffer system, in particular in the form of buffer salt(s) ("component (e)"). In particular, the chemical buffer system is used to set or keep constant the pH value of the composition.

The amounts used of the chemical buffer system can vary within wide ranges. Within the scope of the present invention, it has proven advantageous for composition (e) to comprise the chemical buffer system, based on the composition and calculated as the sum of all components of the chemical buffer system, in an amount in the range of 0.001 to 5 wt %, in particular 0.01 to 4 wt %, especially 0.1 to 3 wt %, preferably 0.5 to 2 wt %, and particularly preferably 1 to 1.5 wt %.

As far as the selection of the buffer system is concerned, this is part of the customary skill of a person skilled in the art. Particularly good results are achieved within the scope of the present invention when the chemical buffer system comprises at least one salt, in particular at least one carboxylic acid salt, especially a citrate, and/or at least one inorganic salt, in particular at least one alkali salt and/or alkaline earth salt, preferably at least one alkali chloride and/or alkaline earth chloride, and particularly preferably sodium chloride. It is particularly preferred when the chemical buffer system is a citrate-based buffer system, or a citrate-based buffer system based on trisodium citrate/trisodium chloride.

According to a preferred embodiment, the chemical buffer system known to a person skilled in the art is used, such as an SSC (saline-sodium citrate) buffer system, based on trisodium citrate (0.3 M at 20 times concentrated SCC) and sodium chloride (3 M at 20 times concentrated SCC). Moreover, it is also possible to use other buffer systems that are well-known to a person skilled in the art, such as HEPES [2-(4-(2-hydroxyethyl) 1-piperazinyl)-ethanesulfonic acid], SSPE [sodium chloride/sodium phosphate/EDTA], PIPES [piperazine-N,N'-bis(2-ethanesulfonic acid)], TMAC [tetramethylammonium chloride], TRIS [tris(hydroxymethyl) aminomethane] or SET buffer.

Particularly good results within the scope of the present invention are additionally achieved when the composition has a pH value in the range of 5.0 to 9.0, in particular in the range of 5.5 to 8.5, especially in the range of 6.0 to 8.0, and preferably in the range of 6.5 to 7.5. The chemical buffer system according to the invention is in particular suitable for setting this pH value and maintaining it during storage and the hybridization reaction.

According to a preferred embodiment of the present invention, it may furthermore be provided that the composition comprises at least one blocking and/or stabilizing agent ("component (f)"), wherein the blocking and/or stabilizing agent in particular is based on nucleic acids and/or nucleic acid analogs, and preferably on DNA and/or RNA. The nucleic acids and/or nucleic acid analogs used as blocking and/or stabilizing agents may, in particular, be locked nucleic acids (LNA) or peptide nucleic acids (PNA). The use of at least one blocking or stabilizing agent is advantageous in several respects since the hybridization probes used can be stabilized, and premature breakdown or premature degradation of the of the probes can be prevented. Additionally, it is possible to minimize non-specific background signals in the signal pattern of the in situ hybridization.

Due to the components used according to the invention, and in particular due to the combination according to the invention of the at least one polar protic or polar aprotic solvent on the one hand, and the at least one carboxylic acid amide, and in particular formamide, on the other hand, respective defined amounts, it is possible to dissolve large amounts of blocking and/or stabilizing agent(s) in the composition according to the invention. It may thus be provided according to the invention that composition (f) comprises the at least one blocking and/or stabilizing agent in a concentration in the range of 0.001 µg/µl to 100 µg/µl, in particular 0.005 µg/µl to 80 µg/µl, especially 0.01 µg/µl to 40 µg/µl, preferably 0.05 µg/µl to 20 µg/µl, and particularly preferably 0.1 µg/µl to 10 µg/µl, based on the composition.

Furthermore, with respect to the compositions according to the invention, it is advantageous when the composition comprises at least one inorganic salt ("component (g)"), in particular alkali salt and/or alkaline earth salt, preferably alkali chloride and/or alkaline earth chloride, and particularly preferably sodium chloride.

The amounts used of the at least one inorganic salt can vary within wide ranges. Particularly good results are achieved by way of the composition according to the present invention when composition (g) comprises the at least one inorganic salt in an amount in the range of 0.01 to 15 wt %, in particular 0.05 to 10 wt %, especially 0.1 to 10 wt %, preferably 0.5 to 5 wt %, and particularly preferably 1 to 3 wt %, based on the composition.

Additionally, surprisingly it was shown that the signal patterns obtained within the scope of the in situ hybridizations can be improved further when the compositions or hybridization solutions according to the invention comprise at least one detergent and/or surfactant ("component (h)"). A detergent or surfactant within the scope of the present invention shall be understood to mean substances capable of lowering the surface tension of liquids or the interfacial tension between two phases. This forms the basis for promoting or improving the formation of dispersions or solutions.

By using at least one detergent or surfactant in the compositions or hybridization solutions according to the invention—without intending to be bound to this theory—the specific hybridization of nucleic acids in the sample and hybridization probes is improved or enhanced. Again without intending to be bound to this theory, the nuclear staining or staining of the cell nucleus usually carried out within the scope of the evaluation or analysis of in situ hybridization samples or preparations is weakened, which, in turn, results in improved contrast of signals with respect to the background and, overall, in greater signal strengths.

Particularly good results are achieved within the scope of the present invention when the detergent and/or surfactant is selected from non-ionic surfactants, preferably polyalkylene glycol ethers, particularly preferably polyalkylene glycol ethers of lauryl alcohol and/or of cetyl alcohol and/or of cetyl stearyl alcohol and/or of oleyl alcohol, and in particular of lauryl alcohol. In this connection, it is particularly preferred when the detergent and/or surfactant is selected from polyoxyethylene (4) lauryl ether, polyoxyethylene (9) lauryl ether and/or polyoxyethylene (23) lauryl ether, and in particular polyoxyethylene (23) lauryl ether.

The amounts of the detergent or surfactant used are variable. It has proven to be particularly advantageous when the composition comprises the at least one detergent and/or surfactant in an amount in the range of 0.001 to 5 wt %, in particular 0.01 to 3 wt %, especially 0.05 to 2 wt %, preferably 0.1 to 1.5 wt %, and particularly preferably 0.12 to 1 wt %, based on the composition.

With respect to the advantageous properties of detergents and surfactants, reference is also made to the exemplary embodiments according to the invention, which prove the positive effects thereof on the hybridization results and/or signal strengths.

As far as the configuration of the composition according to the invention is concerned, it may in particular be provided that this is an aqueous solution. In this connection, it is advantageous for the composition to comprise water, and in particular purified water, in an amount in the range of 10 to 99 wt %, in particular in the range of 20 to 95 wt %, preferably in the range of 30 to 90 wt %, and particularly preferably in the range of 40 to 85 wt %, based on the composition.

Moreover, it may be provided within the scope of the present invention that the composition comprises water in such an amount that the sum, including all components, always results in 100% or 100 wt %, based on the composition.

Furthermore, it may also be provided that the composition comprises water as a carrier or an excipient. Likewise, it may be provided that the composition is aqueous.

According to a particularly preferred embodiment, the present invention thus relates to a composition for use in hybridization, in particular in situ hybridization, and especially automated in situ hybridization, in particular for the identification and/or for the detection of nucleic acids, preferably RNA and/or DNA, in a biological sample, preferably in one or more cells and/or in one or more nuclei, and in particular a composition as described above, the composition comprising:

(a) at least one, preferably locus-specific, hybridization probe ("component (a)"), in particular in a concentration in the range of 0.1 ng/μl to 50 ng/μl, in particular 0.5 ng/μl to 50 ng/μl, especially 0.7 ng/μl to 8 ng/μl, and preferably 1 ng/μl to 5 ng/μl, based on the composition;

(b) at least one polar protic or polar aprotic solvent ("component (b)"), preferably having a cyclic molecule structure, in particular in an amount in the range of 0.5 to 40 vol %, in particular 1 to 35 vol %, especially 2 to 30 vol %, preferably 5 to 20 vol %, and particularly preferably 7 to 15 vol. %, based on the composition;

(c) at least one carboxylic acid amide and/or salts thereof ("component (c)"), in particular formamide and/or salts thereof, in particular in an amount in the range of 10 to 60 vol %, in particular 15 to 50 vol %, especially 17 to 40 vol %, and preferably 20 to 30 vol %, based on the composition;

(d) optionally at least one polysaccharide ("component (d)"), especially a neutral biopolysaccharide, preferably dextran and/or the derivatives or salts thereof, in particular in an amount in the range of 0.1 to 50 wt %, in particular 1 to 40 wt %, especially 5 to 30 wt %, preferably 10 to 20 wt %, and particularly preferably 13 to 18 wt %, based on the composition;

(e) optionally at least one chemical buffer system ("component (e)"), in particular in the form of buffer salt(s), in particular in an amount in the range of 0.001 to 5 wt %, in particular 0.01 to 4 wt %, especially 0.1 to 3 wt %, preferably 0.5 to 2 wt %, and particularly preferably 1 to 1.5 wt %, based on the composition, and calculated as the sum of all components of the chemical buffer system;

(f) optionally, at least one blocking and/or stabilizing agent ("component (f)"), in particular in a concentration in the range of 0.001 μg/μl to 100 μg/μl, in particular 0.005 μg/μl to 80 μg/μl, especially 0.01 μg/μl to 40 μg/μl, preferably 0.05 μg/μl to 20 μg/μl, and particularly preferably 0.1 μg/μl to 10 μg/μl, based on the composition;

(g) optionally at least one inorganic salt ("component (g)"), in particular alkali salt and/or alkaline earth salt, preferably alkali chloride and/or alkaline earth chloride, and particularly preferably sodium chloride, in particular in an amount in the range of 0.01 to 15 wt %, in particular 0.05 to 10 wt %, especially 0.1 to 10 wt %, preferably 0.5 to 5 wt %, and particularly preferably 1 to 3 wt %, based on the composition; and (h) optionally at least one detergent and/or surfactant ("component (h)"), in particular in an amount in the range of 0.001 to 5 wt %, in particular 0.01 to 3 wt %, especially 0.05 to 2 wt %, preferably 0.1 to 1.5 wt %, and particularly preferably 0.12 to 1 wt %, based on the composition.

According to a further particularly preferred embodiment, the present invention furthermore relates to a composition for use in hybridization, in particular in situ hybridization, and especially automated in situ hybridization, in particular for the identification and/or for the detection of nucleic acids, preferably RNA and/or DNA, in a biological sample, preferably in one or more cells and/or in one or more nuclei, preferably a composition as described above, the composition comprising:

(a) at least one, preferably locus-specific, hybridization probe ("component (a)"), in particular in a concentration in the range of 0.1 ng/μl to 50 ng/μl, in particular 0.5 ng/μl to 50 ng/μl, especially 0.7 ng/μl to 8 ng/μl, and preferably 1 ng/μl to 5 ng/μl, based on the composition;

(b) at least one polar protic or polar aprotic solvent ("component (b)"), preferably having a cyclic molecule structure, particularly preferably γ-butyrolactone, 2-pyrrolidone (γ-butyrolactam) and/or ethylene carbonate, and particularly preferably ethylene carbonate, in particular in an amount in the range of 0.5 to 40 vol %, in particular 1 to 35 vol %, especially 2 to 30 vol %, preferably 5 to 20 vol %, and particularly preferably 7 to 15 vol %, based on the composition;

(c) formamide and/or salts thereof ("component (c)"), in particular in an amount in the range of 10 to 60 vol %, in particular 15 to 50 vol %, especially 17 to 40 vol %, and preferably 20 to 30 vol %, based on the composition;

(d) optionally dextran and/or the derivatives or salts thereof ("component (d)"), in particular in an amount in the range of 0.1 to 50 wt %, in particular 1 to 40 wt %, especially 5 to 30 wt %, preferably 10 to 20 wt %, and particularly preferably 13 to 18 wt %, based on the composition;

(e) optionally at least one chemical buffer system, in particular in the form of buffer salt(s), preferably citrate and/or sodium chloride, ("component (e)"), in particular in an amount in the range of 0.001 to 5 wt %, in particular 0.01 to 4 wt %, especially 0.1 to 3 wt %, preferably 0.5 to 2 wt %, and particularly preferably 1 to 1.5 wt %, based on the composition, and calculated as the sum of all components of the chemical buffer system;

(f) optionally, at least one blocking and/or stabilizing agent ("component (f)"), in particular in a concentration in the range of 0.001 μg/μl to 100 μg/μl, in particular 0.005 μg/μl to 80 μg/μl, especially 0.01 μg/μl to 40 μg/μl, preferably 0.05 μg/μl to 20 μg/μl, and particularly preferably 0.1 μg/μl to 10 μg/μl, based on the composition;

(g) optionally at least one inorganic salt ("component (g)"), in particular alkali salt and/or alkaline earth salt, preferably alkali chloride and/or alkaline earth chloride, and particularly preferably sodium chloride, in particular in an amount in the range of 0.01 to 15 wt %, in particular 0.05 to 10 wt %, especially 0.1 to 10 wt %, preferably 0.5 to 5 wt %, and particularly preferably 1 to 3 wt %, based on the composition; and (h) optionally at least one polyalkylene glycol ether ("component (h)"), in particular in an amount in the range of 0.001 to 5 wt %, in particular 0.01 to 3 wt %, especially 0.05 to 2 wt %, preferably 0.1 to 1.5 wt %, and particularly preferably 0.12 to 1 wt %, based on the composition.

As is apparent from the comments above, it is possible, for the first time, to stabilize even small amounts of hybridization probes or hybridizations probes in low concentrations in compositions for use in in situ hybridization, based on the purposeful combination according to the invention. The compositions according to the invention are suitable both for use in automated in situ hybridization processes and in situ hybridization processes having short or flexible hybridization durations, such as rapid ISH, and result in signal patterns that can be evaluated well and have strong signals. Compositions of this kind are not yet known from the prior art.

The compositions according to the invention can, in particular, be used for in situ hybridizations in connection with the diagnosis and/or prognosis of diseases, in particular malignant tumors, preferably carcinomas, sarcomas and/or leukemia.

The genes to be examined in this connection are preferably selected from the group consisting of ALK, ROS1, RET, NRG1, NTRK1, CARS, EML4, FGFR2, FGFR3, KIF5B, TGF, BCR, ABL, ALK, BCL2, BCL6, BIRC3, CCND1, EGR1, ETV6, FGFR1, FGFR3, IGH, KMT2A, MYC, PML, RARA, RUNX1, RUNX1T1, EWSR1, CHOP, FUS, COL1A1, DDIT3, JAZF1, NR4A3, FOXO1, FUS, PAX3, PAX7, PDGFB, SS18, TFE3, USP6, WT1, HER2/ERBB2, FGFR1, ALK, CCND1, CDK4, CD274, PDCD1LG2, EGR1, EGFR, ESR1, ETV1, FGF3,4,19, FGFR2, FGFR3, FHIT (RCC), KRAS, MDM2, MDM4, MET, MYB, MYC, MYCN, PIK3CA, PTEN, SMARCB1, SOX2, TERT, TOP2A, TP53, TYMS and/or VHL.

Particularly good results are achieved within the scope of the present invention when the compositions according to the invention are used to detect chromosomal aberrations based on inversions and/or translocations.

In this connection, the compositions according to the invention can, in particular, be used to detect different translocations and/or inversions, in particular lung tumors, wherein in particular the genes ALK, ROS1, RET, NRG1, NTRK1, CARS, EML4, FGFR2, FGFR3, KIF5B and/or TGF are affected.

Furthermore, it may be provided that the composition according to the invention is used to detect different translocations and/or inversions, in particular in lymphomas and leukemia, wherein in particular the genes BCR, ABL, ALK, BCL2, BCL6, BIRC3, CCND1, EGR1, ETV6, FGFR1, FGFR3, IGH, KMT2A, MYC, PML, RARA, RUNX1 and/or RUNX1T1 are affected.

According to a further preferred embodiment of the present invention, the composition according to the invention can be used to detect different translocations and/or inversions, in particular in sarcomas, wherein in particular the genes EWSR1, CHOP, FUS, COL1A1, DDIT3, JAZF1, NR4A3, FOXO1, FUS, PAX3, PAX7, PDGFB, SS18, TFE3, USP6 and/or WT1 are affected.

It may also be provided according to the invention to use the composition for detecting inversions and/or translocations, wherein in particular genes ALK and ROS1 are affected.

Within the scope of a preferred embodiment of the present invention, the composition according to the invention can also be used to detect different translocations and/or inversions, in particular in lung tumors, wherein in particular the genes ALK, ROS1, RET, NRG1, NTRK1, CARS, EML4, FGFR2, FGFR3, KIF5B and/or TGF are affected.

Furthermore, it may be provided that the composition according to the invention is used to detect different translocations and/or inversions, in particular in lymphomas and leukemia, wherein in particular the genes BCR, ABL, ALK, BCL2, BCL6, BIRC3, CCND1, EGR1, ETV6, FGFR1, FGFR3, IGH, KMT2A, MYC, PML, RARA, RUNX1 and/or RUNX1T1 are affected.

According to a further preferred embodiment of the present invention, the composition according to the invention is used to detect different translocations and/or inversions, in particular in sarcomas, wherein in particular the genes EWSR1, CHOP, FUS, COL1A1, DDIT3, JAZF1, NR4A3, FOXO1, FUS, PAX3, PAX7, PDGFB, SS18, TFE3, USP6 and/or WT1 are affected.

It may also be provided according to the invention to use the composition according to the invention for detecting inversions and/or translocations, wherein in particular the genes ALK and ROS1 are affected.

Furthermore—according to a second aspect according to the invention—the present invention relates to the use of a composition, as described above, during hybridization, in particular in situ hybridization, preferably automated in situ hybridization, in particular for the identification and/or for the detection of nucleic acids, preferably RNA and/or DNA, in a biological sample, preferably in one or more cells and/or in one or more nuclei.

For more in-depth details regarding the use according to the invention, reference may be made to the above comments on the first aspect of the invention, related to the composition according to the invention, which apply accordingly with respect to the use according to the invention.

According to a third aspect of the present invention, the present invention moreover relates to a method for detecting nucleic acids, preferably RNA and/or DNA, and/or chromosomal aberrations in a biological sample, preferably in one or more cells and/or in one or more nuclei by way of hybridization, in particular in situ hybridization, and preferably automated in situ hybridization, using a composition, as described above.

Within the scope of the present invention, surprisingly it was found that the use of the compositions according to the invention in the, in particular automated, hybridization method according to the invention, in particular in situ hybridization method, results in good signal patterns having strong signals that can be evaluated well. Moreover, using the compositions according to the first aspect of the invention, the method according to the invention for the detection of nucleic acids can, surprisingly, also be carried out with short hybridization times, without this resulting in a decrease in the signal intensity or strength.

According to this aspect of the present invention, the present invention in particular relates to a method for detecting nucleic acids, preferably RNA and/or DNA, and/or chromosomal aberrations in a biological sample, preferably in one or more cells and/or in one or more nuclei by way of hybridization, in particular in situ hybridization, and preferably automated in situ hybridization, the method comprising the following steps:

(a) providing a biological sample, in particular based on one or more cells and/or one or more nuclei, preferably in the form of tissue, for in situ hybridization;

(b) providing a composition for use in the hybridization, wherein the composition comprises at least one, preferably locus-specific, hybridization probe ("component (a)"), at least one polar protic or polar aprotic solvent, preferably having a cyclic molecule structure, ("component (b)"), and at least one carboxylic acid amide and/or salts thereof, in particular formamide and/or salts thereof, in an amount greater than 10 vol %, based on the composition ("component (c)"), in particular a composition as described above;

(c) bringing the biological sample from method step (a) in contact with the composition from method step (b);

(d) denaturing the biological sample from method step (a) and the composition from method step (b), wherein the biological sample and the composition are denatured separately from one another, in particular prior to carrying out method step (c), or jointly, in particular after carrying out after method step (c);

(e) subsequently hybridizing the at least one, preferably locus-specific, hybridization probe comprised in the composition and the nucleic acids comprised in the biological samples; and (f) subsequently detecting the hybridized, preferably locus-specific, hybridization probes and/or the nucleic acids to be detected in the biological sample.

According to a particularly preferred embodiment of the method according to the invention, it may be provided that the method is carried out on or in an automated system and/or automatically. Based on this, the efficiency or the sample throughput of hybridization processes, and in particular of in situ hybridizations, can be significantly increased.

As far as specifically method step (a), or the provision of a biological sample for carrying out the method according to the invention, and in particular the in situ hybridization, is concerned, this takes place in a manner known to a person skilled in the art, which is to say the biological samples are prepared in the known manner for the in situ hybridization. In particular, method step (a) comprises fixing and embedding the samples based on cells or tissues, applying the samples onto suitable carriers, pretreating the samples and drying the samples. A person skilled in the art is essentially familiar with the provision or preparation of samples for in situ hybridization processes, so that no further comments are required at this point.

In connection with method step (b), or the provision of the composition, reference is made to the above aspects of the invention, and in particular to the comments in connection with the composition according to the present invention, to avoid unnecessary repetition.

As far as, beyond that, method step (b) is concerned, it has proven advantageous when the composition is used in an amount in the range of 0.1 to 5,000 μl, in particular 1 to 2,500 μl, especially 2 to 1,500 μl, preferably 5 to 1,000 μl, particularly preferably 10 to 500 μl, most particularly preferably 20 to 250 μl, and still more preferably 40 to 150 μl. The aforementioned amounts of the composition result in high-quality signal patterns that can be evaluated well, both with automated or automatic in situ hybridizations, and with in situ hybridizations having short hybridization durations. The composition is, in particular, used in an amount that suffices to cover the examined sample area.

Method step (d) for denaturing the nucleic acids in the biological sample and in the composition takes place in a manner that is essentially known to a person skilled in art. Within the scope of the method according to the invention, the biological sample on the one hand, and the composition on the other hand, may be subjected to the denaturing process according to method step (e) separately from one another prior to being brought in contact with one another. Likewise, it may be provided to subject the biological sample and the composition jointly to a co-denaturing process after method step (c) has been carried out. Setting the denaturing conditions, and in particular the necessary temperature, is known per se to a person skilled in the art and does not require further comments. In particular, the temperature in method step (d) may be in the range of 60 to 90° C., and preferably in the range of 70 to 85° C.

Method step (e), which is used to hybridize the, preferably locus-specific, hybridization probes present in the hybridization compositions on the one hand, and the DNA or chromosome portions to be detected present in the biological samples on the other hand, is also carried out in the manner essentially known to a person skilled in art. No comments are necessary at this point, in particular as far as setting a suitable hybridization temperature is concerned.

In connection with method step (e), it has furthermore, surprisingly, been found within the scope of the present invention that the hybridization, which is to say the annealing of the, preferably locus-specific, hybridization probes to the DNA or chromosome section to be detected, may be improved yet again when method step (e) is carried out with movement, in particular a wave-like and/or continuous movement.

Within the scope of the present invention, it was furthermore, surprisingly, shown that the method according to the invention, using the compositions according to the invention, leads to excellent results both with short hybridization durations ("rapid ISH"), such as 10 to 240 min, and with the customarily used long hybridization durations, such as 4 to 100 h.

It may be provided within the scope of the present invention, that the hybridization or method step (e) within the scope of the method according to the invention is carried out over a duration in the range of 10 min to 240 min, in particular in the range of 30 min to 180 min, especially in the range of 60 min to 150 min, and preferably in the range of 90 min to 130 min. Moreover, it may also be provided that the hybridization or method step (e) is carried out over a duration in the range of 1 h to 100 h, in particular 2 h to 80 h, especially 3 h to 50 h, preferably 4 h to 30 h, particularly preferably 5 h to 25 h, and still more preferably 8 h to 20 h.

The detection of the bound or hybridized, preferably locus-specific, hybridization probes in the biological sample likewise takes place by way of methods that are known per se to a person skilled in the art, as a function of the labeling of the hybridization probes. No further comments are required in this regard. Within the scope of the method according to the invention, preferably fluorescent-labeled hybridization probes (fluorescence ISH (FISH)), which are detected by way of fluorescence microscopy, or antigen-labeled probes, and in particular hapten-labeled probes, are used, which are visualized using antibodies by way of color reactions and detected by way of light microscopy (bright field ISH (BrISH), chromogenic ISH (CISH), silver-enhanced ISH (SISH)). It is obvious to a person skilled in the art just how exactly the detection of the labeled hybridization probes used is to take place within the scope of the method according to the invention.

For more in-depth details regarding the method according to the invention, reference may be made to the above comments on the above aspects of the invention, which apply accordingly to the method according to the invention.

Finally—according to a fourth aspect of the present invention—the present invention relates to a kit or kit of parts or system for detecting nucleic acids, preferably RNA and/or DNA, and/or chromosomal aberrations in a biological sample, preferably in one or more cells and/or in one or more nuclei by way of hybridization, in particular in situ hybridization, and preferably automated in situ hybridization, wherein the kit includes a composition, as described above, and/or wherein the kit is intended and/or used and/or suitable for carrying out the above-described method.

According to a preferred embodiment, it may be provided according to the invention that the kit according to the invention includes the components of the composition, as described above, in a shared storage vessel or application device or in storage vessels and/or application devices that are spatially separated and different from one another.

For more in-depth details regarding the kit according to the invention, reference may be made to the above comments on the above aspects of the invention, which apply accordingly to the kit according to the invention.

BRIEF DESCRIPTION OF THE DRAWINGS

Further features, advantages, and special characteristics of the present invention will be apparent from the following description of preferred embodiments based on FIGS. 1 to 4. In the drawings.

DETAILED DESCRIPTION OF THE DRAWINGS

To enhance the depiction in black and white, the figures shown here are not fluorescence images of the test results described below, but diagrams prepared, among other things, based on the respective observed results.

Figure 1:
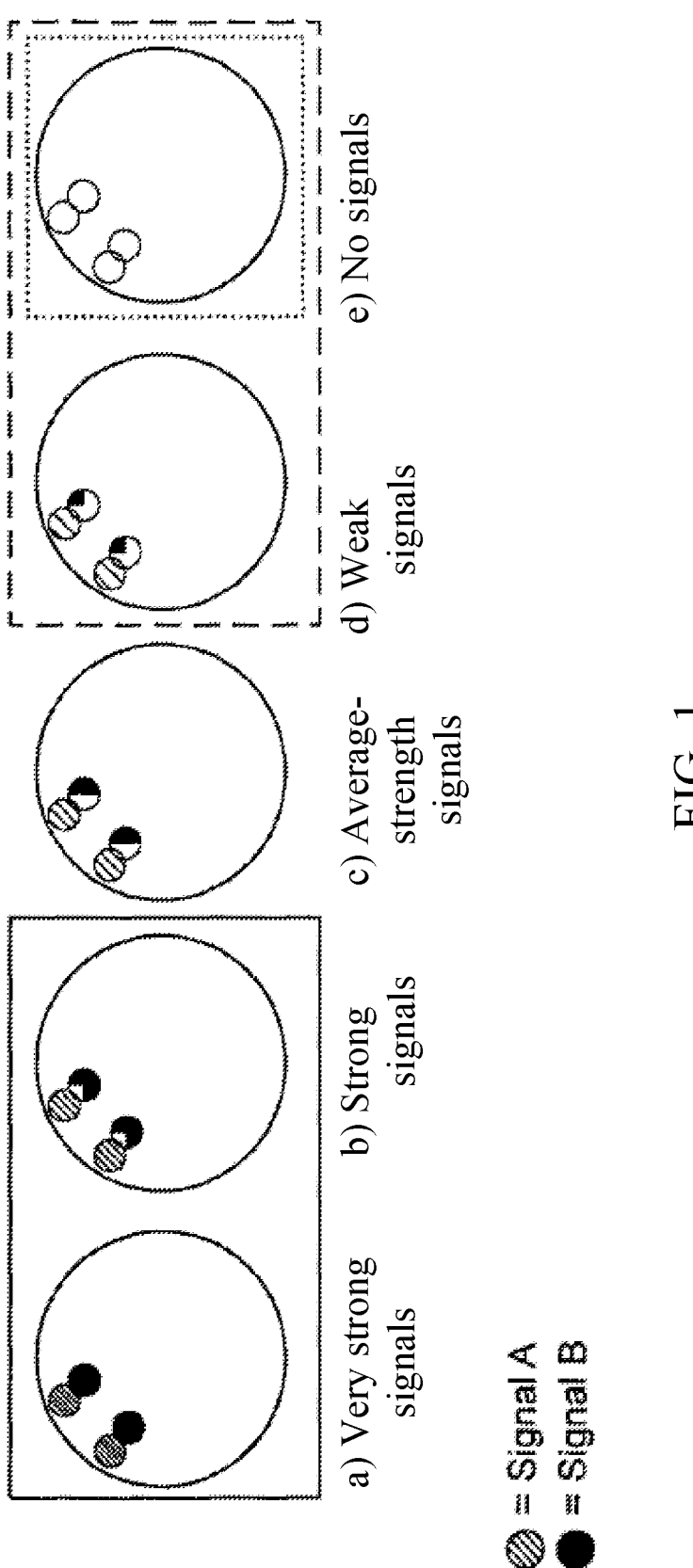
FIG. 1 shows a schematic illustration of in situ hybridization results regarding the signal patterns, and in particular the signal strength.

FIG. 1 shows a schematic illustration of in situ hybridization results (by way of example for FISH, BrISH and CISH), which allow conclusions to the drawn of the signal pattern obtained, and in particular of the signal strengths. Locus-specific hybridization probes that may be used are in particular probes that are used specifically for genomic areas of the human genes HER2, ALK or ROS1.

In principle, diploid cells are assumed within the scope of the present invention, which is to say two signals are obtained, or a double signal is obtained, in cells without aberrations for each detected genomic region. The signal strengths obtained are divided into the following five graduated stages: a) very strong signals; b) strong signals; c) average-strength signals; d) weak signals; e) no signals; see FIG. 1. Hereafter, examples of signal patterns, and in particular of signal strengths, of in situ hybridizations using standard hybridization solutions on the one hand, and hybridization solutions according to the invention on the other hand, or of in situ hybridizations using the method according to the invention and using standard methods are shown.

The methods and compositions according to the invention based on specific concentrations of formamide and polar protic or polar aprotic solvent having a cyclic molecule structure result in very strong or strong signals (FIG. 1, see stages a) and b)). These excellent signal patterns are observed both with flexible in situ hybridizations, which is to say in situ hybridizations having a two-hour hybridization duration ("rapid ISH") or having a 16-hour hybridization duration, and with automated methods for carrying out the in situ hybridization. The signal strength can be seen as a result of both the brightness and of the contrast with respect to the background (for example, strong background results in weaker contrast and thus in less strong signals).

Compositions or hybridization solutions that comprise a polar protic or polar aprotic solvent having a cyclic molecule structure, but that do not comprise formamide, do not result in hybridization signals (FIG. 1, see stage e)). Compositions or hybridization solutions that comprise formamide, but do not comprise polar protic or polar aprotic solvent having a cyclic molecule structure, likewise do not result in hybridization signals, or at most result in very weak or hardly detectable hybridization signals (FIG. 1, see stages e) and f)).

Figure 2:
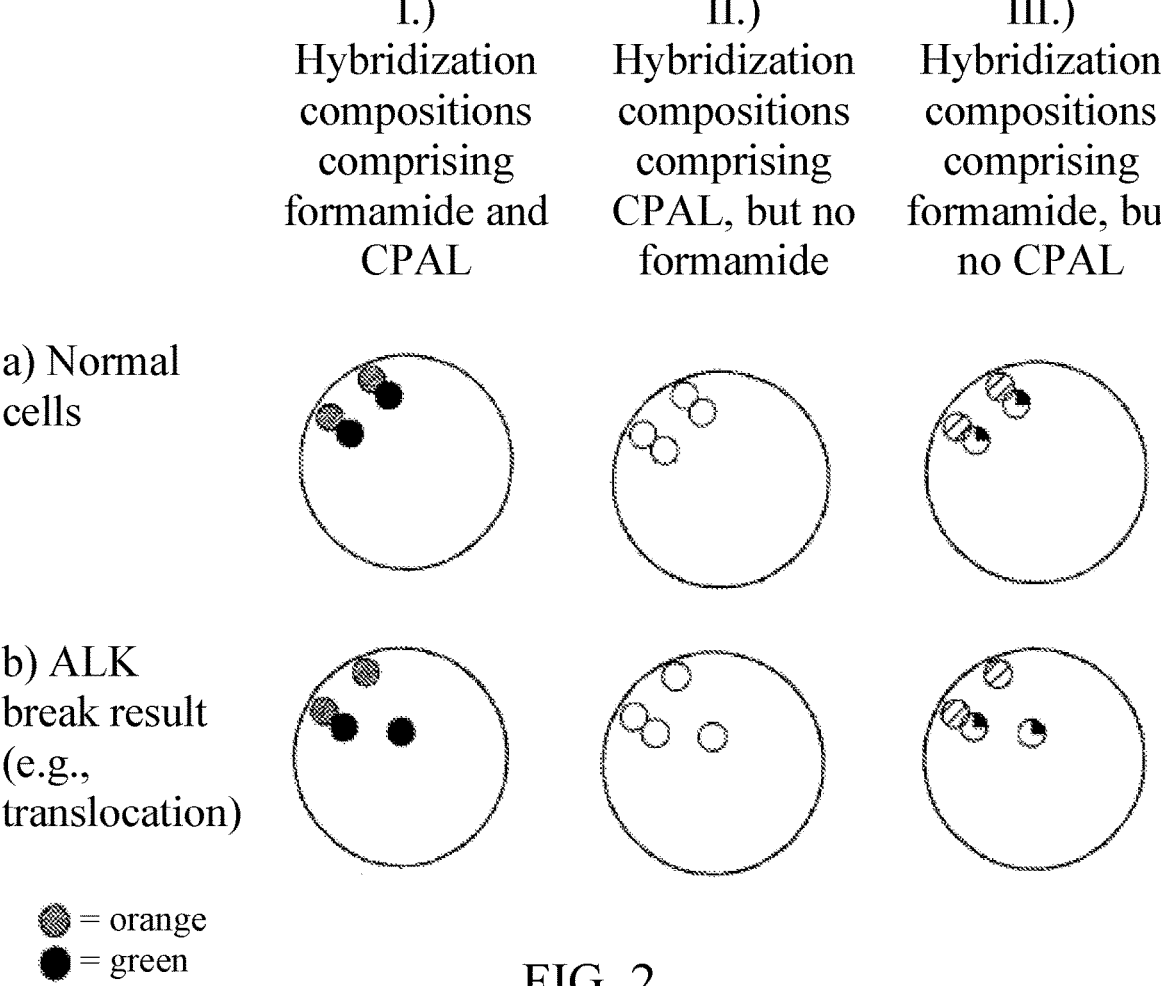
FIG. 2 shows a schematic illustration of the signal patterns, and in particular the signal strengths, when using a FISH probe "Auto ALK Break Apart Probe" within the scope of in situ hybridizations, using stainers.

FIG. 2 shows a schematic illustration of the signal patterns and signal strengths of in situ hybridizations carried out using a FISH probe "Auto ALK Break Apart Probe" on a stainer. This locus-specific hybridization probe is composed of green-labeled polynucleotides (excitation at 503 nm and emission at 528 nm), which in 2p23 are directed against sequences situated proximal to the ALK breakpoint region, and orange-labeled polynucleotides (excitation at 547 nm and emission at 572 nm), which in 2p23 are directed against sequences situated distal to the ALK breakpoint region. The hybridization solution or composition is based on the components listed below: 18 wt % dextran sulfate, 600 mM NaCl, 22 vol % formamide, 1× concentrated SSC buffer, 12.5 wt % ethylene carbonate, blocking and stabilizing DNA in a concentration of 0.1 µg/µl, and locus-specific hybridization probes in a concentration of 2 ng/µl, each based on the hybridization solution or composition.

After the denaturing process (20 minutes at 75° C.), the hybridization probe is hybridized over a hybridization or renaturing duration of 120 minutes at 45° C. in an automated system (Celerus Wave RPD System) under constant wave movement of the glass slides with cell and tissue samples.

When suitable filter sets are used, the hybridization signals for the non-rearranged ALK gene appear as green-orange fluorescent fusion signals. In the interphase of a normal cell (without ALK aberration), two green/orange double signals or fusion signals appear when using a suitable green/orange dual bandbass filter set (FIG. 2, see column/row I/a). A 2p23 locus affected by an ALK translocation is marked by a separate green signal and a separate orange signal (FIG. 2, see column/row I/b).

The resulting signal strengths, and thus the ability to evaluate the results, decisively depend on the specific concentrations of the polar protic or polar aprotic solvents having a cyclic molecule structure (CPAL) and of the formamide in the underlying hybridization solutions of the hybridization probes. Low concentrations of the polar protic or polar aprotic solvents having a cyclic molecule structure (CPAL), such as ethylene carbonate here, between 5 wt % and 13 wt %, and formamide concentrations of greater than 10 vol %, result in very strong fluorescent signals and very low background (FIG. 2, see column I). Comparison compositions containing no formamide lead to results that cannot be evaluated, which is to say no gene-specific signals can be generated (FIG. 2, see column II). Comparison compositions containing no polar protic or polar aprotic solvent having a cyclic molecule structure, such as ethylene carbonate, result in very weak signals that are consequently difficult to evaluate (FIG. 2, see column III).

Figure 3:
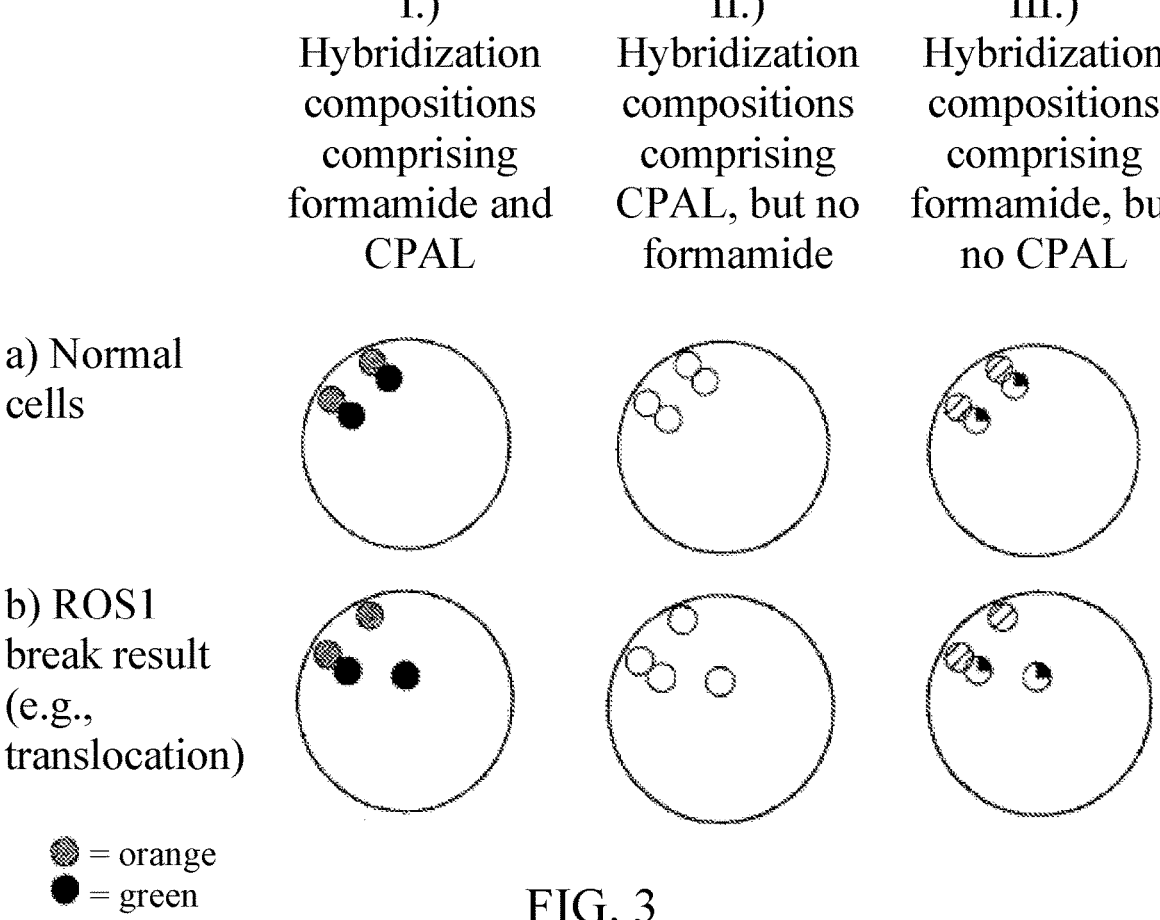
FIG. 3 shows a schematic illustration of the signal patterns, and in particular the signal strengths, when using a flexible FISH probe "Flexible ROS1 Break Apart Probe" within the scope of in situ hybridizations.

FIG. 3 shows a schematic illustration of the signal patterns and signal strengths of in situ hybridizations carried out using a FISH probe "Flexible ROS1 Break Apart Probe." This locus-specific hybridization probe is composed of green-labeled polynucleotides (excitation at 503 nm and emission at 528 nm), which in 26q22 are directed against sequences situated proximal to the ROS1 breakpoint region, and orange-labeled polynucleotides (excitation at 547 nm and emission at 572 nm), which in 6q22 are directed against sequences situated distal to the ROS1 breakpoint region. The hybridization solution or composition is based on the following components: 15 wt % dextran sulfate, 500 mM NaCl, 27 vol % formamide, 1× concentrated SSC buffer, 9.75 wt % ethylene carbonate, blocking and stabilizing DNA in a concentration of 2 μg/μl and locus-specific hybridization probes in a concentration of 5 ng/μl, each based on the hybridization solution or composition. After the denaturing process (10 minutes at 75° C.), the hybridization probes are hybridized over a hybridization or renaturing duration of 10 minutes either for 2 hours at 37° C., or for 16 hours at 37° C., with cell and tissue samples.

When suitable filter sets are used, the hybridization signals for the non-rearranged ROS1 gene appear as green/orange fluorescent signals. In the interphase of a normal cell (without ROS1 aberration), two green/orange fusion signals or double signals appear when using a suitable green/orange dual bandbass filter set (FIG. 3, see column/row I/a). A 2p6q22 locus affected by an ROS1 translocation is marked by a separate green signal and a separate orange signal (FIG. 3, see column/row I/b).

The resulting signal strengths, and thus the ability to evaluate the results, decisively depend on the specific concentrations of the polar protic or polar aprotic solvents having a cyclic molecule structure (CPAL) and of the formamide in the underlying hybridization solutions of the locus-specific hybridization probe. Low concentrations of the polar protic or polar aprotic solvents having a cyclic molecule structure (CPAL), such as ethylene carbonate here, in the range of 5 wt % and 13 wt %, and formamide concentrations of more than 10 wt %, result in very strong fluorescent signals and very low background, both after a hybridization time of two hours and of 16 hours (FIG. 3, see column I). The hybridization solutions achieve excellent results with respect to the signal strength, both with a short and with a long hybridization duration.

Comparison compositions that comprise a polar protic or polar aprotic solvent having a cyclic molecule structure, but that do not comprise formamide, do not lead to results that can be evaluated, both after a two-hour and after a 16-hour hybridization duration, which is to say no gene-specific signals can be generated (FIG. 3, see column II). Comparison compositions containing formamide, but no polar protic or polar aprotic solvent having a cyclic molecule structure (CPAL), result in very weak signals (FIG. 3, see column III).

Figure 4:
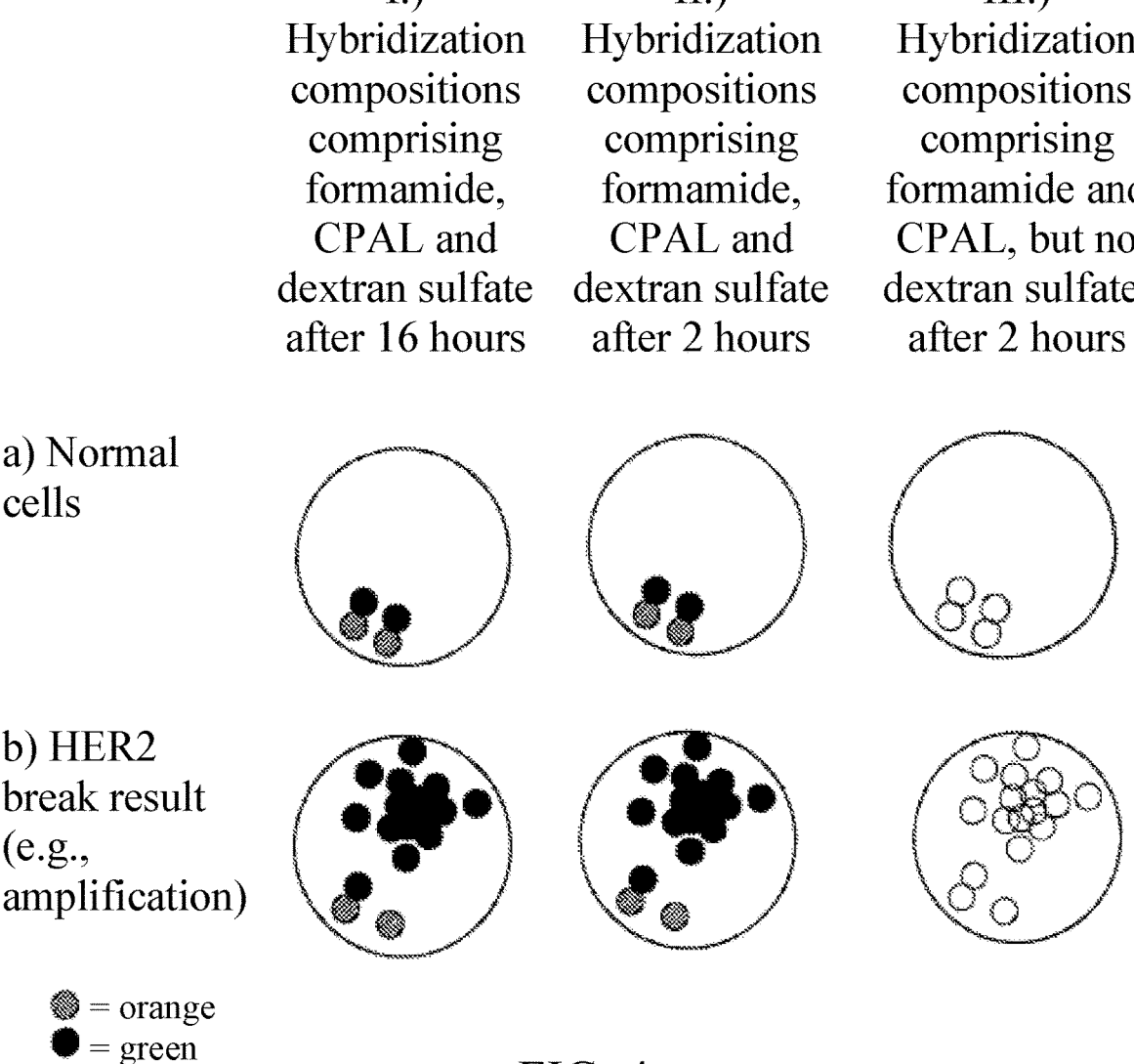
FIG. 4 shows a schematic illustration of the signal patterns, and in particular the signal strengths, when using a flexible FISH probe "Flexible HER2/CEN17 Probe" within the scope of in situ hybridizations.

FIG. 4 shows a schematic illustration of the signal patterns and signal strengths of in situ hybridizations carried out using a flexible FISH probe "Flexible HER2/CEN17 Probe." This probe is composed of green-labeled polynucleotides (excitation at 503 nm and emission at 528 nm), which are directed against region 17q11.2-q12 of the HER2 gene, and orange-labeled polynucleotides (excitation at 547 nm and emission at 572 nm), which are directed against the alpha satellite centromeric region of chromosome 17 (D17Z1) The hybridization solution comprises the components listed below: 15 wt % dextran sulfate, 500 mM NaCl, 27 vol % formamide, 1× concentrated SSC buffer, 10.5 wt % ethylene carbonate, blocking and stabilizing DNA in a concentration of 2 μg/μl and locus-specific hybridization probes in a concentration of 5 ng/μl probe DNA, each based on the composition. After denaturing (10 minutes at 75° C.), the hybridization probes are hybridized either for two hours at 37° C., or for 16 hours at 37° C., with cell and tissue samples.

When using suitable filter sets, the hybridization signals for the non-rearranged HER2 gene appear in the generated signal pattern as two green fluorescent signals, and the hybridization signals for the non-rearranged centromeric region of chromosome 17 appear as two orange fluorescent signals. In the interphase of a normal cell without HER2 aberration and without aberrations of chromosome 17, two green and two orange signals appear when using a suitable green/orange dual bandbass filter set (FIG. 4, see column/row I/a and II/a). A 17q11.2-q12 locus affected by an HER2 amplification is marked by additional green signals (FIG. 4, see column/row I/b and II/b).

The resulting signal strengths, and thus the ability to evaluate the results, decisively depend on the presence of dextran sulfate in the underlying hybridization solutions or compositions. Hybridization solutions that comprise a polar protic or polar aprotic solvent having a cyclic molecule structure, such as ethylene carbonate, in an amount in the range of 5 wt % to 13 wt %, formamide in an amount of at least 10 wt %, and dextran sulfate in an amount of 15 wt %, allow very strong fluorescent signals and very low background to be achieved within the scope of the in situ hybridizations, both with short and with long hybridization durations of two and 16 hours, respectively (FIG. 4, see columns I and II). Hybridization solutions containing no dextran sulfate lead to results that cannot be evaluated, which is to say no gene-specific signals can be generated (FIG. 4, see column III).

EXEMPLARY EMBODIMENTS

A) Prior to describing individual, and in particular particularly preferred exemplary embodiments of the present invention, initially the underlying in situ hybridization methods per se will be described.

Example A.1 ISH Procedure I (Flexible FISH Having Hybridization Durations of Two Hours or 16 Hours)

The reagents used to carry out the "flexible" rapid FISH came from the ZytoLight Flexible FISH-Tissue Implementation Kit (Z-2182-20, ZytoVision GmbH, Bremerhaven, Germany). The kit comprises the necessary reagents (Heat Pretreatment Solution Citric, Pepsin Solution, 5 times concentrated flexible FISH wash buffer and DAPI/DuraTect™ solution) for carrying out the FISH on formalin-fixed and paraffin-embedded tissue sections.

The FISH was carried out on 3 to 5 μm thick sections of formalin-fixed paraffin-embedded (FFPE) tissue from mammary carcinoma, lung tissue, lymph node tissue, kidney tissue, prostate tissue and placenta tissue. The tissue sections were mounted on coated glass slides and baked overnight at 58° C.

To remove the paraffin, the preparations were incubated twice for five minutes each at room temperature (RT) in 100% xylene. Thereafter, a descending ethanol series was carried out at room temperature for two minutes each (twice each 96%, 90%, 70% denature ethanol). After two incubation steps, each lasting two minutes, in ultrapure water at room temperature, the heat pretreatment followed over a duration of 20 minutes at 98° C. in Heat Pretreatment Solution Citric, followed by two more incubation steps for two minutes each in ultrapure water at RT. The proteolytic pretreatment was carried out by grafting Pepsin Solution (RTU) onto the preparations and subsequently incubating these in a moist chamber at 37° C. for a duration of 5 to 30 minutes. The digestion step was followed by two incubation steps, lasting two minutes each, at RT in ultrapure water and an ascending ethanol series (70%, 90%, 96%) for one minute each at RT.

After the preparations were air dried, 10 μl of a hybridization solution, which contained fluorescent-labeled hybridization probes, was pipetted directly onto the sections. After a suitable cover slip was placed on, the preparations were sealed using Fixogum and stored on a heating plate for ten minutes at 75° C. for co-denaturing. For hybridization, the preparations were transferred into a preheated moist chamber and incubated at 37° C. for either two hours or over night (approximately 16 hours).

Prior to the stringency wash, the Fixogum was removed, and the preparations were incubated for approximately 2 minutes at RT in 1× concentrated flexible wash buffer. Thereafter, the cover slip was removed, the actual wash was carried out by incubation in 1× concentrated flexible wash buffer for a duration of ten minutes at 72° C., and further incubation over three minutes at RT. This was followed by an ascending ethanol series (70%, 90%, 96%) for one minute each at RT before the preparations were air dried, wherein drying took place in the absence of light. Afterwards, DAPI DuraTect Solution was applied, and the preparation was provided with a cover slip.

The evaluation was carried out by way of a fluorescent microscope (Axio Scope.A1 with lighting unit HXP 120V, Carl Zeiss Microscopy GmbH) and appropriate filter sets for the respective underlying excitation and emission ranges.

Example A.2 ISH Procedure II (Automated FISH on the Automated System Celerus Wave RPD System)

The reagents used to carry out the automated fish (on the automated system Celerus Wave RPD System from Celerus Diagnostics, California, USA) were contained in the LRM Bin (Celerus Diagnostics, California, USA). The LRM (Linear Reagent Magazine) contained all the necessary reagents for the heat pretreatment, the proteolysis and the washing buffer for the required washing steps. DAPI/DuraTect™ (ZytoVision GmbH, Bremerhaven, Germany) was used to cover the preparations and stain the cell nuclei. The automated system probe was located in the PAC Bin, which was inserted into the LRM Bin.

The automated FISH was carried out on 3 to 5 μm thick formalin-fixed and paraffin-embedded (FFPE) human tissue sections obtained from mammalian cancer, lungs, lymph nodes, kidneys, prostate and/or placenta, which were mounted on coated glass slides and baked overnight at 58° C. To remove the paraffin, the preparations were treated according to the predefined program of the Celerus Wave® RPD System. This was followed by the heat pretreatment for 15 minutes at 95° C., followed by two incubation steps in washing buffer for six minutes at 40°. After drying for 10 minutes at 45° C., the proteolytic pretreatment followed. This was carried out using pepsin by incubating the preparations over a duration in the range of 5 to 40 minutes at 60° C. The digestion step was followed by two incubation steps, lasting four minutes each, in ultrapure water at 37° C. and a drying step of seven minutes at 50° C.

After drying, the fluorescent-labeled locus-specific hybridization probe, which was comprised in the hybridization solution, was applied. For this purpose, 130 μl of the hybridization solution per glass slide was applied to the preparations. Co-denaturing took place over a duration of ten minutes at 80° C., and subsequent hybridization took place for 120 minutes at 42° C. The hybridization was accompanied by permanent movements of the glass slides, and thus wave-like movements of the hybridization solution.

After the hybridization, the washing step was carried out for four minutes at 37° C. using washing buffer.

The stringency wash took place over a duration of 15 minutes at 45° C. A subsequent washing step again took place for four minutes at 37° C. Afterwards, a drying process followed for five minutes at 45° C. on the automated system. The preparations were removed from the automated system after these steps had been automatically carried out. This was followed by an ascending ethanol series (70%, 90%, 96%) for one minute each at RT before the preparations were air dried in the absence of light. Finally, the cell nuclei were stained using the stain 4',6-diamidino-2-phenylindole (DAPI) by applying DAPI DuraTect Solution (ZytoVision GmbH, Bremerhaven), and the preparation was provided with a cover slip.

The evaluation was carried out by way of a fluorescent microscope (Axio Scope.A1 with lighting unit HXP 120V, Carl Zeiss Microscopy GmbH) and appropriate filter sets for the respective underlying excitation and emission ranges.

Example A.3 ISH Procedure III (Automated FISH on the Automated System Pathcom Stainer)

The reagents used to carry out the automated FISH (on the automated system Pathcom Stainer from PathCom Systems Cooperation, California, USA) came from the ISH Detection Kit (PathCom Systems Corporation, Sierra Ct, Dublin, USA). The kit contained all the necessary reactions (Dewax Solutions, Retrieval Solution, Pepsin, diH₂O) for carrying out the automated FISH. Additionally, the PathCom Systems Wash Buffer for IHC and ISH was needed. DAPI/DuraTect™ Solution (ZytoVision GmbH, Bremerhaven, Germany) was used to cover the preparations and stain the cell nuclei.

The automated FISH was carried out on 3 to 5 μm thick formalin-fixed and paraffin-embedded (FFPE) human tissue sections, such as from mammalian cancer, lungs, lymph nodes, kidneys, prostate and/or placenta, which were mounted on coated glass slides and baked overnight at 58° C.

To remove the paraffin, the preparations were initially treated with a first Dewax Solution over a duration of six minutes at 65°. Afterwards, the preparations were treated with four additional Dewax Solutions for six minutes each at 62° C., and finally with a final Dewax Solution for six minutes at 50°. This was followed by a heat pretreatment using the Retrieval Solution, initially for 15 minutes at 98° C., and thereafter for eight minutes at 65° C., so that the entire heat pretreatment lasted approximately 23 minutes. After two incubation steps using a washing buffer ("Wash Buffer") for six minutes each at 40° C., a drying step is carried out for ten minutes at 45° C. The drying process was followed by a proteolytic pretreatment. This took place by incubating the preparations in pepsin over a duration in the range of 5 to 40 minutes at 37° C. The digestion step was followed by three incubation steps, lasting three minutes each, in ultrapure water at 37° C. and a subsequent drying step for ten minutes at 50° C.

After drying, 110 μl hybridization solution, which contained fluorescent-labeled locus-specific hybridization probes, was applied to the preparations. The sample and hybridization solution were co-denatured over a duration of 20 minutes at 75° C. The hybridization or renaturing following denaturing was carried out over a duration of 120 minutes at 45° C., continuously moving the hybridization solution as a result of induced movements of the reaction chambers in the automated system.

After hybridization, the washing step took place for four minutes at 37° C. using washing buffer ("Wash Buffer"). The stringency wash was carried out over a duration of 15 minutes at 45° C. A subsequent washing step again took place for four minutes at 37° C. Afterwards, a drying process followed for five minutes at 45° C. on the automated system. The preparations were removed from the automated system after these steps had been automatically carried out. This was followed by an ascending ethanol series (70%, 90%, 96%) for one minute each at RT before the preparations were air dried in the absence of light. Finally, the cell nuclei were stained using the stain 4',6-diamidino-2-phenylindole (DAPI) by applying DAPI DuraTect™ Solution (ZytoVision GmbH, Bremerhaven), and the preparation was provided with a cover slip.

The evaluation was carried out by way of a fluorescent microscope (Axio Scope.A1 with lighting unit HXP 120V, Carl Zeiss Microscopy GmbH) and appropriate filter sets for the respective underlying steering excitation and emission ranges.

B) Hereafter, embodiments according to the invention, and in particular particularly preferred embodiments of the present invention and comparative in situ hybridizations will be described:

Example B.1 FISH for Detecting Gene-Specific HER2 Signals in a "Flexible" Rapid FISH Process Using the locus-specific hybridization probe "Flexible HER2/CEN17 Probe," gene-specific HER2 signals were generated or detected with the aid of a "flexible" rapid FISH process, which can be carried out using both short hybridization durations of two hours and using overnight hybridization lasting 16 hours. The hybridization per se was carried out according to the above-described ISH procedure I (Flexible FISH having hybridization durations of two hours or 16 hours).

The hybridization probe was composed of green-labeled polynucleotides (excitation at 503 nm and emission at 528 nm), which are directed against region 17q11.2-q12 of the HER2 gene, and orange-labeled polynucleotides (excitation at 547 nm and emission at 572 nm), which are directed against the alpha satellite centromeric region of chromosome 17 (D17Z1)

Hybridization solution I: 15 wt % dextran sulfate, 500 mM NaCl, 27 vol % formamide, 1× concentrated SSC buffer, 12 wt % ethylene carbonate, 2 μg/μl blocking and stabilizing DNA and 5 ng/μl locus-specific hybridization probe, each based on the composition.

Hybridization solution II: 15 wt % dextran sulfate, 500 mM NaCl, 27 vol % formamide, 1× concentrated SSC buffer, 10.5% wt % ethylene carbonate, 2 μg/μl blocking and stabilizing DNA and 5 ng/μl locus-specific hybridization probe, each based on the composition.

The two hybridization solutions I and II led to excellent results, which is to say very strong signals, in equal measure. Very strong gene-specific HER2 signals were found, in addition to likewise very strong CEN17-specific signals, very low background and a well-preserved structure of the cells and tissue, both with short hybridization durations of two hours and with long hybridization durations of 16 hours. This was observed not only with normal cells/tissue or cells/tissue without aberrations on chromosome 17, but also with cells/tissue, in particular from mammalian cancer, having HER2 amplification. In this way, it was possible to clearly detect the HER2 amplifications to be identified by way of the hybridization probe, which were identified in the signal pattern based on the occurrence of multiple HER2-specific signals or HER2 signal clusters (see FIG. 4).

Example B.2 Influence of the Formamide Concentration on Flexible Rapid FISH Processes Using the locus-specific hybridization probe "Flexible HER2/CEN17 Probe" for the above-described ISH procedure I, the influence of the formamide concentration in the hybridization solutions on the signal strength was examined.

The hybridization probe was composed of green-labeled polynucleotides (excitation at 503 nm and emission at 528 nm), which are directed against region 17q11.2-q12 of the HER2 gene, and orange-labeled polynucleotides (excitation at 547 nm and emission at 572 nm), which are directed against the alpha satellite centromeric region of chromosome 17 (D17Z1)

Hybridization solution I: 15 wt % dextran sulfate, 500 mM NaCl, 27 vol % formamide, 1× concentrated SSC buffer, 10.5 wt % ethylene carbonate, 2 μg/μl blocking and stabilizing DNA and 5 ng/μl locus-specific hybridization probe, each based on the composition.

Compared to hybridization solution I, hybridization solutions II to V have different formamide concentrations of 14 vol % (II), 11 vol % (III), 7 wt % (IV) and 0 vol % (V).

Hybridization solutions I to V were each used within the scope of the above-described ISH procedure I, using both short hybridization durations of two hours and long hybridization durations of 16 hours, wherein the hybridization probe "Flexible HER2/CEN17 Probe" was employed. The signal patterns obtained in this regard were compared to one another, in particular with respect to the respective achieved signal strength.

Very strong gene-specific HER2 signals were found with hybridization solution I (27 vol formamide), in addition to likewise very strong CEN17-specific signals, very low background and a well-preserved structure of cells and tissue, both with short and with long hybridization durations.

After the two-hour hybridization durations, lower formamide concentrations resulted in weaker or no HER2-specific signals. At 14 vol % formamide (solution II), strong signals were generated, which could still be evaluated very well. At 11 vol % formamide (solution III), in contrast, only average-strength signals were generated in the signal patterns. Hybridization solutions containing 7 vol % formamide (solutions IV) resulted only in weak signals, which no longer allowed any evaluation. No signals were obtained with hybridization solutions containing no formamide (solution V).

Even with long hybridization durations of 16 hours, decreasing formamide concentrations resulted in decreasing signal strengths in the hybridization solutions with respect to the HER2-specific signals. At 14 vol % formamide (solution II), very strong signals were generated, which could still be evaluated very well. At 11 vol % formamide (solution III), likewise, strong signals that could still be evaluated well were generated in the signal patterns. Hybridization solutions containing 7 vol % formamide (solutions IV) resulted only in weak signals, which no longer allowed any evaluation. No signals were obtained with hybridization solutions containing no formamide (solution V).

Example B.3 Influence of the Ethylene Carbonate Concentration on Flexible Rapid FISH Processes Using the locus-specific hybridization probe "Flexible HER2/CEN17 Probe" for the above-described ISH procedure I, the influence of the ethylene carbonate concentration in the hybridization solutions on the signal strength was examined.

The hybridization probe was composed of green-labeled polynucleotides (excitation at 503 nm and emission at 528 nm), which are directed against region 17q11.2-q12 of the HER2 gene, and orange-labeled polynucleotides (excitation at 547 nm and emission at 572 nm), which are directed against the alpha satellite centromeric region of chromosome 17 (D17Z1)

Hybridization solution I: 15 wt % dextran sulfate, 500 mM NaCl, 27 vol % formamide, 1× concentrated SSC buffer, 10.5 wt % ethylene carbonate, 2 µg/µl blocking and stabilizing DNA and 5 ng/µl probe DNA, each based on the composition.

Compared to hybridization solution I, hybridization solutions II to IV had different ethylene carbonate concentrations of 7 vol % (II), 5 wt % (III) and 0 wt % (IV).

Hybridization solutions I to IV were each used within the scope of the above-described ISH procedure I, using both short hybridization durations of two hours and long hybridization durations of 16 hours, wherein the hybridization probe "Flexible HER2/CEN17 Probe" was employed. The signal patterns obtained in this regard were compared to one another, in particular with respect to the respective achieved signal strength.

Very strong gene-specific HER2 signals were found with hybridization solution I (10.5 wt % ethylene carbonate), in addition to likewise very strong CEN17-specific signals, very low background and a well-preserved structure of cells and tissue, both with short and with long hybridization durations.

After the two-hour hybridization durations, lower ethylene carbonate concentrations resulted in weaker or no HER2-specific signals. At 7 wt % ethylene carbonate (solution II), strong signals were generated, which could still be evaluated very well. At 5 wt % ethylene carbonate (solution III), in contrast, only average-strength signals were generated in the signal patterns. Only very weak signals that could no longer be evaluated were obtained with hybridization solutions containing no ethylene carbonate (solution IV).

Even with long hybridization durations of 16 hours, decreasing ethylene carbonate concentrations resulted in decreasing signal strengths in the hybridization solutions with respect to the HER2-specific signals. At 7 wt % ethylene carbonate (solution II), very strong signals were generated. At 5 vol % ethylene carbonate (solution III), likewise very strong signals were generated in the signal patterns. Only average-strength signals were obtained with hybridization solutions containing no ethylene carbonate (solution IV).

Example B.4 Influence of Dextran Sulfate on Flexible Rapid FISH Processes

Using the locus-specific hybridization probe "Flexible HER2/CEN17 Probe" for the above-described ISH procedure I, the influence of dextran sulfate in the hybridization solutions on the signal strength was examined. Reference was made to the above comments in connection with the execution of the hybridization and the specificity of the probes.

Hybridization solution I: 15 wt % dextran sulfate, 500 mM NaCl, 27 vol % formamide, 1× concentrated SSC buffer, 10.5 wt % ethylene carbonate, 2 µg/µl blocking and stabilizing DNA and 5 ng/µl probe DNA, each based on the composition.

Hybridization solution II: 500 mM NaCl, 27 vol % formamide, 1× concentrated SSC buffer, 10.5 wt % ethylene carbonate, 2 µg/µl blocking and stabilizing DNA and 5 ng/µl probe DNA, each based on the composition.

The signal patterns received with hybridization solutions I and II were compared to one another, in particular with respect to the respective achieved signal strength.

Very strong gene-specific HER2 signals, in addition to likewise very strong CEN17-specific signals, very low background and a well-preserved structure of the cells and tissue were found in the signal patterns obtained with hybridization solution I, both with short and with long hybridization durations. Hybridization solution II without dextran sulfate resulted in no visible or detectable signals with short hybridization durations. With long hybridization durations, only very weak or no visible or detectable signals were obtained with hybridization solution II.

Example B.5 Influence of Various Polar Protic or Polar Aprotic Solvents Having a Cyclic Molecule Structure on Flexible Rapid FISH Processes Using the locus-specific hybridization probe "Flexible HER2/CEN17 Probe" for the above-described ISH procedure I, the influence of various polar protic or polar aprotic solvents having a cyclic molecule structure in the hybridization solutions on the signal strength was examined. Reference is made to the above comments in connection with the execution of the hybridization and the specificity of the probes.

Hybridization solution I: 15 wt % dextran sulfate, 500 mM NaCl, 27 vol % formamide, 1× concentrated SSC buffer, 10.5 wt % ethylene carbonate (I), 2 µg/µl blocking and stabilizing DNA and 5 ng/µl probe DNA, each based on the composition.

Hybridization solution II: 10.5 wt % 2-piperidone (valerolactam) instead of ethylene carbonate.

Hybridization solution III: 10.5 vol % 2-pyrrolidone (γ-butyrolactam) instead of ethylene carbonate.

Hybridization solution IV: 10.5 vol % 3-sulfolene (butadiene sulfone) instead of ethylene carbonate.

Hybridization solution V: 10.5 vol % γ-butyrolactone instead of ethylene carbonate.

The signal patterns received with hybridization solutions I to V were compared to one another, in particular with respect to the respective achieved signal strength.

Very strong gene-specific HER2 signals were found with all hybridization solutions I to V, which is to say with all tested polar protic or polar aprotic solvents having a cyclic molecule structure, in addition to likewise very strong CEN17-specific signals, very low background and a well-preserved structure of cells and tissue, both with short and with long hybridization durations. The best results were achieved with 2-pyrrolidone (γ-butyrolactam), γ-butyrolactone and ethylene carbonate; however, very good results were also achieved with 2-piperidone (valerolactam) and 3-sulfolene ("butadiene sulfone").

These results were observed both with normal cells/tissue or cells/tissue without aberrations on chromosome 17, and with cells/tissue, in particular from mammalian cancer, having HER2 amplification. In this way, the HER2 amplifications to be identified could also be clearly identified with all respective individually used polar protic or polar aprotic solvents having a cyclic molecule structure.

Example B.6 FISH for Detecting Gene-Specific ALK Signals in Automated FISH Processes Hybridization solutions based on formamide and ethylene carbonate, which contained "Auto ALK Break Apart Probe"

as the locus-specific hybridization probe, were used to detect ALK-specific signals in automated FISH processes. The FISH per se was carried out according to above-described ISH procedure II (automated FISH on the automated system Celerus Wave RPD System).

The locus-specific hybridization probe was composed of green-labeled polynucleotides (excitation at 503 nm and emission at 528 nm), which in 2p23 were directed against sequences situated proximal to the ALK breakpoint region, and orange-labeled polynucleotides (excitation at 547 nm and emission at 572 nm), which in 2p23 were directed against sequences situated distal to the ALK breakpoint region.

Hybridization solution: 18 wt % dextran sulfate, 600 mM NaCl, 22 vol % formamide, 1× concentrated SSC buffer, 12.75 wt % ethylene carbonate, 0.1 µg/µl blocking and stabilizing DNA and 2 ng/µl locus-specific hybridization probe, each based on the composition.

In the signal pattern obtained, very strong ALK-specific signals, very low background and a well-preserved structure of the cells and tissue were found. This was observed both with normal cells/tissue or cells/tissue without aberrations on chromosome 2, and also with cells/tissue with ALK aberrations. In this way, it was possible to clearly identify the ALK aberrations to be identified by way of the hybridization probe (which is to say break apart events of green-orange fusion signals).

Example B.7 Influence of the Formamide Concentration on Automated FISH Processes Using the locus-specific hybridization probe "Auto HER2/CEN17 Probe" for the above-described ISH procedure III, the influence of the formamide concentration in the hybridization solutions on the signal strength was examined.

The locus-specific hybridization probe was composed of orange-labeled polynucleotides (excitation at 547 nm and emission at 572 nm), which are directed against region 17q11.2-q12 of the HER2 gene, and green-labeled polynucleotides (excitation at 503 nm and emission at 528 nm), which are directed against the alpha satellite centromeric region of chromosome 17 (D17Z1)

Hybridization solution I: 18 wt % dextran sulfate, 600 mM NaCl, 21 vol % formamide, 1× concentrated SSC buffer, 12.75% wt % ethylene carbonate, 0.1 µg/µl blocking and stabilizing DNA and 2 ng/µl hybridization probe, each based on the composition.

Compared to hybridization solution I, hybridization solutions II to V had different formamide concentrations of 17 vol % (II), 13 vol % (III), 9 vol % (IV) and 0 vol % (V).

Very strong gene-specific HER2 signals (in addition to likewise very strong CEN17-specific signals), very low background and a well-preserved structure of the cells and tissue were detected with hybridization solution I. Very strong signals were also obtained with hybridization solution II (17 vol % formamide). Hybridization solution III containing 13 vol % formamide still resulted in strong signals, while that containing 9 vol % (hybridization solution IV) yielded only average-strength signals. No signals were obtained with hybridization solutions (hybridization solution V) that contained no formamide.

Example B.8 Influence of the Ethylene Carbonate Concentration on Automated FISH Processes Using the locus-specific hybridization probe "Auto HER2/CEN17 Probe" for the above-described ISH procedure III, the influence of the ethylene carbonate concentration in the hybridization solutions on the signal strength was examined. In connection with the execution of the hybridization and the specificity of the probes, reference was made to the above comments in connection with the hybridization probe "Auto HER2/CEN17 Probe."

Hybridization solution I: 18 wt % dextran sulfate, 600 mM NaCl, 21 vol % formamide, 1× concentrated SSC buffer, 12.75% wt % ethylene carbonate, 0.1 µg/µl blocking and stabilizing DNA and 2 ng/µl hybridization probe, each based on the composition.

Compared to hybridization solution I, hybridization solutions II to IV had different ethylene carbonate concentrations of 9 vol % (II), 6 wt % (III) and 0 wt % (IV).

Very strong gene-specific HER2 signals (in addition to likewise very strong CEN17-specific signals), very low background and a well-preserved structure of the cells and tissue were detected with hybridization solution I. Only average-strength signals were obtained with hybridization solution II (9 wt % ethylene carbonate). Hybridization solutions III and IV containing 6 vol % ethylene carbonate and containing no ethylene carbonate, respectively, resulted only in weak signals that could no longer be evaluated.

Example B.9 Influence of Dextran Sulfate on Automated FISH Processes

Using the locus-specific hybridization probe "Auto ROS1 Break Apart Probe" for the above-described ISH procedure II (automated FISH on the automated system Celerus Wave RPD System), the influence of dextran sulfate in the hybridization solutions on the signal strength was examined. Reference is made to the above comments with respect to procedure II in connection with the execution of the hybridization.

The hybridization probe was composed of green-labeled polynucleotides (excitation at 503 nm and emission at 528 nm), which in 26q22 were directed against sequences situated proximal to the ROS1 breakpoint region, and orange-labeled polynucleotides (excitation at 547 nm and emission at 572 nm), which in 6q22 were directed against sequences situated distal to the ROS1 breakpoint region.

Hybridization solution I: 18 wt % dextran sulfate, 600 mM NaCl, 22 vol % formamide, 1× concentrated SSC buffer, 12.75 wt % ethylene carbonate, 0.1 µg/µl blocking and stabilizing DNA and 2 ng/µl locus-specific hybridization probes, each based on the composition.

Compared to hybridization solution I, hybridization solution II did not contain any dextran sulfate. Very strong gene-specific ROS1 signals, very low background and a well-preserved structure of cells and tissue were achieved with hybridization solution I. No visible or detectable signals were achieved with hybridization solution II, which contains the hybridization probe in a composition without dextran sulfate.

Example B.10 Influence of Various Select Polar Protic or Polar Aprotic Solvents Having a Cyclic Molecule Structure on Automated FISH Processes Using the locus-specific hybridization probe "Auto HER2/CEN17 Probe" for the above-described ISH procedure III (automated FISH on the automated system Pathcom Stainer), the influence of various polar protic or polar aprotic solvents having a cyclic structure in the hybridization solutions on the signal strength was examined. ISH procedure III (see above comments regarding ISH procedure III) was carried out, using the automated system Pathcom Stainer. To avoid unnecessary repetition, reference is made to above comments with respect to specificity and labeling of the hybridization probe "Auto HER2/CEN17 Probe."

Hybridization solutions I to V: 18 wt % dextran sulfate, 600 mM NaCl, 22 vol % formamide, 1× concentrated SSC buffer, 12.75 wt % or vol % (depending on substance used) of a polar protic or polar aprotic solvent having a cyclic structure, 0.1 µg/µl blocking and stabilizing DNA, and 2 ng/µl hybridization probe, each based on the composition, wherein the polar protic or polar aprotic solvent having a cyclic structure used was either ethylene carbonate (I, wt %), 2-piperidone (valerolactam) (II, wt %), 2-pyrrolidone (γ-butyrolactam) (III, vol %), 3-sulfolene ("butadiene sulfone") (IV, wt %), and γ-butyrolactone (V, vol %)

Strong to very strong gene-specific HER2 signals (in addition to likewise strong to very strong CEN17-specific signals), very low background and a well-preserved structure of the cells and tissue were found with all tested polar protic or polar aprotic solvents having a cyclic structure within the scope of the in situ hybridizations. Only minor differences were found with respect to the intensity of the signals in the following graduated stages from very strong to respectively slightly weaker: γ-butyrolactone, 2-pyrrolidone (γ-butyrolactam), ethylene carbonate, 2-piperidone (valerolactam) and 3-sulfolene ("butadiene sulfone"). These results could be observed both with normal cells/tissue or cells/tissue without aberrations on chromosome 17, and with cells/tissue, in particular mammalian cancer, having HER2 amplification. In this way, the HER2 amplification to be detected (which is to say either multiple HER2-specific signals or HER2 signal clusters) could also be clearly identified with all respective individually used polar protic or polar aprotic solvents having a cyclic structure.

Example B.11 Influence of Movement on Hybridization in Automated FISH Processes

Using the locus-specific hybridization probe "Auto HER2/CEN17 Probe" for the above-described ISH procedure III, the influence of in particular wave-like movements during the hybridization step of automated in situ hybridizations on the resulting signal pattern was examined. For this purpose, the above-described ISH procedure III was carried out on the automated system "Pathcom Stainer" using the hybridization probe "Auto HER2/CEN17 Probe."

In connection with the specificity of the probes, reference is made to the above comments in connection with the hybridization probe "Auto HER2/CEN17 Probe."

The hybridization solutions contained the 18 wt % dextran sulfate, 600 mM NaCl, 21 vol % formamide, 1× concentrated SSC buffer, 12.75 wt % ethylene carbonate, 0.1 µg/µl blocking and stabilizing DNA, and 2 ng/µl locus-specific hybridization probes.

For comparison purposes, ISH procedure III was carried out with movement, in particular wave-like movement, of the samples and hybridization composition or solution, and without movement of the samples and hybridization composition or solution, during the hybridization. The hybridization took place in each case for 120 minutes at 45° C.

The movement of the samples or hybridization solutions took place continuously by moving the reaction chambers of the automated system. The movement of the reaction chamber was induced at intervals of 15 seconds, two minutes and 10 minutes, with a respective opening time of the cover the hybridization chamber of one second. For comparison purposes, the hybridization of the samples was carried out without movement and without opening the hybridization chamber.

All approaches carried out with movement and with opening of the hybridization chamber yielded very strong gene-specific HER2 signals (in addition to likewise very strong CEN17-specific signals), very low background and a well-preserved morphology of cells and tissue. The excellent results were obtained in equal measure for movement intervals of 15 seconds, two minutes, and 10 minutes. Signals or signal patterns that were easy to evaluate were likewise obtained without movement of hybridization solutions or samples; however, the signals turned out to be weaker than with the hybridizations conducted with movement of the hybridization solutions or samples.

Example B.12 Influence of Detergents on Hybridization in Automated FISH Processes Using the locus-specific hybridization probe "Auto ROS1 Break Apart Probe" for the above-described ISH procedure III (automated FISH on the automated system Pathcom Stainer), the influence of the polyalkylene glycol ether Brij®-35 (synonymously also referred to as Brij®-L23 or polyoxyethylene (23) lauryl ether) in the hybridization solutions on the signal strength was examined. In connection with the execution of the hybridization according to ISH procedure III and the specificity of the hybridization probe "Auto ROS1 Break Apart Probe," reference is made to above comments.

Hybridization solution I: 18 wt % dextran sulfate, 600 mM NaCl, 22 vol % formamide, 1× concentrated SSC buffer, 9.95 wt % ethylene carbonate, 0.1 µg/µl blocking and stabilizing DNA and 2 ng/µl locus-specific hybridization probes, each based on the composition.

Compared to hybridization solution I, hybridization solutions II to VI had different Brij®-35 concentrations of 0.125 wt % (II), 0.2 wt % (III), 0.4 wt % (IV), 0.9 wt % (V), and 1.8 wt % (VI), each based on the composition.

Strong gene-specific ROS1 signals, low background and a well-preserved structure of cells and tissue were achieved with hybridization solution I (without Brij®-35).

Very strong signals were obtained with hybridization solutions II to V (Brij®-35 concentrations of 0.125 wt % to 0.9 wt %). These stronger signals compared to hybridization solution I (without Brij®-35)—without intending to be bound to this theory-could be attributed to weaker nucleus staining associated with the use of the detergent, and thus better contrast (signal to background).

Only average-strength signals were obtained for hybridization solutions containing the detergent Brij®-35 in a concentration of 1.8 wt % (hybridization solution VI), based on the composition.

PREFERRED EMBODIMENTS

In embodiments that are preferred according to the invention, the invention relates to:
1. A composition, and in particular a composition for use in hybridization, in particular in situ hybridization, preferably automated in situ hybridization, in particular for the identification and/or for the detection of nucleic acids, preferably RNA and/or DNA, in a biological sample, preferably in one or more cells and/or in one or more nuclei,
the composition comprising:
(a) at least one, preferably locus-specific, hybridization probe ("component (a)");

(b) at least one polar protic or polar aprotic solvent ("component (b)"), preferably having a cyclic molecule structure; and (c) at least one carboxylic acid amide and/or salts thereof ("component (c)"), in particular formamide and/or salts thereof, in an amount of more than 10 vol %, based on the composition.

2. The composition according to embodiment 1, wherein composition (a) comprises the at least one, preferably locus-specific, hybridization probe in a concentration in the range of 0.1 ng/µl to 50 ng/µl, in particular 0.5 ng/µl to 50 ng/µl, especially 0.7 ng/µl to 8 ng/µl, and preferably 1 ng/µl to 5 ng/µl, based on the composition; and/or wherein (b) the at least one polar protic or polar aprotic solvent is selected from the group consisting of solvents having lactone, sulfone, nitrile, carbonate and/or amide functionality; and/or wherein (b) the at least one polar aprotic or polar protic solvent is selected from the group consisting of ethylene carbonate, pyrrolidones, lactams, ethylene sulfite, γ-butyrolactone, ethylene trithiocarbonate, propylene carbonate and/or sulfolane, in particular ethylene carbonate and/or pyrrolidones, and preferably ethylene carbonate; and/or wherein (b) the at least one solvent, preferably having a cyclic molecule structure, is a polar aprotic solvent, in particular selected from cyclic carbonates (cyclic carbonate esters), in particular cyclic carbonate esters of alkylene glycols, preferably ethylene carbonate (1,3-dioxolan-2-one) and propylene carbonate, and particularly preferably ethylene carbonate, and cyclic monothiocarbonates, dithiocarbonates and trithiocarbonates, and in particular ethylene sulfite and ethylene trithiocarbonate; and/or wherein (b) the at least one solvent, preferably having a cyclic molecule structure, is a polar aprotic solvent, in particular selected from aprotic cyclic amides (lactams), in particular N-alkyl-substituted pyrrolidones, and preferably n-methyl-2-pyrrolidone and/or N-ethyl-2-pyrrolidone; and/or wherein (b) the at least one solvent, preferably having a cyclic molecule structure, is a polar protic solvent, in particular selected from protic cyclic amides (lactams), in particular protic cyclic amides (lactams) having a hydrogen atom on the amide nitrogen (lactam nitrogen), preferably from the group consisting of 2-pyrrolidone (γ-butyrolactam), 3-pyrrolidone, caprolactams and/or 2-piperidone (valerolactam), particularly preferably pyrrolidones, and most particularly preferably 2-pyrrolidone (γ-butyrolactam); and/or wherein (b) that the at least one solvent is a polar protic solvent having a cyclic molecule structure, wherein the cyclic molecule structure comprises an N-heterocycle having a free hydrogen atom at the nitrogen atom; and/or wherein (b) the at least one polar protic or polar aprotic solvent, preferably having a cyclic molecule structure, is selected from the group consisting of γ-butyrolactone, 2-pyrrolidone (γ-butyrolactam) and/or ethylene carbonate.

3. The composition according to embodiment 1 or 2, wherein the composition (b) comprises the at least one polar protic or polar aprotic solvent, preferably having a cyclic molecule structure, in an amount that does not result in the denaturing of nucleic acids, and/or wherein the composition (b) comprises the at least one polar protic or polar aprotic solvent, preferably having a cyclic molecule structure, in an amount in the range of 0.5 to 40 vol % or wt %, in particular 1 to 35 vol % or wt %, especially 2 to 30 vol % or wt %, preferably 5 to 20 vol % or wt %, and particularly preferably 7 to 15 vol % or wt %, based on the composition; and/or wherein the composition (b) comprises the at least one polar protic or polar aprotic solvent, preferably having a cyclic molecule structure, in an amount of at least 0.5 vol % or wt %, in particular at least 1 vol % or wt %, especially at least 2 vol % or wt %, preferably at least 5 vol % or wt %, particularly preferably at least 7 vol % or wt %, and most particularly preferably at least 10 vol % or wt %, and/or wherein the composition (b) comprises the at least one polar protic or polar aprotic solvent, preferably having a cyclic molecule structure, in an amount of no more than 50 vol % or wt %, in particular no more than 40 vol % or wt %, especially no more than 30 vol % or wt %, preferably no more than 20 vol % or wt %, particularly preferably no more than 15 vol % or wt %, and most particularly preferably no more than 13 vol % or wt %, based on the composition.

4. The composition according to any one of the preceding embodiments, wherein the composition (c) comprises the at least one carboxylic acid amide and/or salts thereof, and in particular formamide and/or salts thereof, in an amount that results in the denaturing of nucleic acids and/or wherein the composition (c) comprises the at least one carboxylic acid amide and/or salts thereof, and in particular formamide and/or salts thereof, in an amount in the range of 10 to 60 vol %, in particular 15 to 50 vol %, especially 17 to 40 vol %, and preferably 20 to 30 vol %, based on the composition; and/or wherein the composition (c) comprises the at least one carboxylic acid amide and/or salts thereof, and in particular formamide and/or salts thereof, in an amount of at least 10 vol %, in particular at least 15 vol %, especially at least 17 vol %, and preferably at least 20 vol %, based on the composition, and/or wherein the composition (c) comprises the at least one carboxylic acid amide and/or salts thereof, and in particular formamide and/or salts thereof, in an amount of no more than 60 vol %, in particular no more than 50 vol %, especially no more than 40 vol %, and preferably no more than 30 vol %, based on the composition; and/or where the composition comprises component (b) and component (c) or the at least one polar protic or polar aprotic solvent, preferably having a cyclic molecule structure, and the at least one carboxylic acid amide and/or salts thereof, and in particular formamide and/or salts thereof, in a volume-based ratio in the range of 1:100 to 50:1, in particular 1:50 to 20:1, especially 1:25 to 10:1, preferably 1:10 to 5:1, particularly preferably 1:5 to 1:1, and most particularly preferably 1:3 to 1:2.

5. The composition according to any one of the preceding embodiments, wherein the composition comprises at least one polysaccharide ("component (d)"), in particular a biopolysaccharide, especially a neutral biopolysaccharide, preferably dextran and/or the derivatives or salts thereof, and particularly preferably dextran sulfate, in particular wherein the composition comprises component (d) in an amount in the range of 0.1 to 50 wt %, in particular 1 to 40 wt %, especially 5 to 30 wt %, preferably 10 to 20 wt %, and particularly preferably 13 to 18 wt %, based on the composition.

6. The composition according to any one of the preceding embodiments, wherein the composition comprises at least one chemical buffer system, in particular in the form of buffer salt(s) ("component (e)");

in particular, wherein the chemical buffer system is used to set and/or keep constant the pH value of the composition; and/or in particular, wherein the composition (e) comprises the chemical buffer system, based on the composition and calculated as the sum of all components of the chemical buffer system, in an amount in the range of 0.001 to 5 wt %, in particular 0.01 to 4 wt %, especially 0.1 to 3 wt %, preferably 0.5 to 2 wt %, and particularly preferably 1 to 1.5 wt %; and/or in particular, wherein the chemical buffer system comprises at least one salt, in particular at least one carboxylic acid salt, especially a citrate, and/or at least one inorganic salt, in particular at least one alkali salt and/or alkaline earth salt, preferably at least one alkali chloride and/or alkaline earth chloride, and particularly preferably sodium chloride; and/or wherein the chemical buffer system is a citrate-based buffer system and/or a citrate-based buffer system based on trisodium citrate/trisodium chloride; and/or wherein the composition has a pH value in the range of 5.0 to 9.0, in particular in the range of 5.5 to 8.5, especially in the range of 6.0 to 8.0, and preferably in the range of 6.5 to 7.5.

7. The composition according to any one of the preceding embodiments, wherein the composition comprises at least one blocking and/or stabilizing agent ("component (f)"), in particular wherein the blocking and/or stabilizing agent is based on nucleic acids, preferably on DNA and/or RNA, in particular wherein the composition (f) comprises the at least one blocking and/or stabilizing agent in a concentration in the range of 0.001 μg/μl to 100 μg/μl, in particular 0.005 μg/μl to 80 μg/μl, especially 0.01 μg/μl to 40 μg/μl, preferably 0.05 μg/μl to 20 μg/μl, and particularly preferably 0.1 μg/μl to 10 μg/μl, based on the composition; and/or wherein the composition comprises at least one inorganic salt ("component (g)"), in particular alkali salt and/or alkaline earth salt, preferably alkali chloride and/or alkaline earth chloride, and particularly preferably sodium chloride, in particular wherein the composition (g) comprises the at least one inorganic salt in an amount in the range of 0.01 to 15 wt %, in particular 0.05 to 10 wt %, especially 0.1 to 10 wt %, preferably 0.5 to 5 wt %, and particularly preferably 1 to 3 wt %, based on the composition.

8. The composition according to any one of the preceding embodiments, wherein the composition comprises at least one detergent and/or surfactant ("component (h)"), in particular wherein the detergent and/or surfactant is selected from non-ionic surfactants, preferably polyalkylene glycol ethers, particularly preferably polyalkylene glycol ethers of lauryl alcohol and/or of cetyl alcohol and/or of cetyl stearyl alcohol and/or of oleyl alcohol, and in particular of lauryl alcohol, and/or in particular wherein the detergent and/or surfactant is selected from polyoxyethylene (4) lauryl ether, polyoxyethylene (9) lauryl ether and/or polyoxyethylene (23) lauryl ether, and in particular polyoxyethylene (23) lauryl ether, and/or in particular wherein the composition comprises the at least one detergent and/or surfactant in an amount in the range of 0.001 to 5 wt %, in particular 0.01 to 3 wt %, especially 0.05 to 2 wt %, preferably 0.1 to 1.5 wt %, and particularly preferably 0.12 to 1 wt %, based on the composition; and/or wherein the composition comprises water, and in particular purified water, in an amount in the range of 10 to 99 wt %, in particular in the range of 20 to 95 wt %, preferably in the range of 30 to 90 wt %, and particularly preferably in the range of 40 to 85 wt %, based on the composition, and/or wherein the composition comprises water as a carrier (excipient) and/or wherein the composition is aqueous and/or wherein the composition comprises water in such an amount that the sum, including all components, always results in 100% or 100 wt %, based on the composition.

9. A composition, and in particular a composition for use in hybridization, in particular in situ hybridization, preferably automated in situ hybridization, in particular for the identification and/or for the detection of nucleic acids, preferably RNA and/or DNA, in a biological sample, preferably in one or more cells and/or in one or more nuclei, preferably a composition according to any one of the preceding embodiments, the composition comprising:

(a) at least one, preferably locus-specific, hybridization probe ("component (a)"), in particular in a concentration in the range of 0.1 ng/μl to 50 ng/μl, in particular 0.5 ng/μl to 50 ng/μl, especially 0.7 ng/μl to 8 ng/μl, and preferably 1 ng/μl to 5 ng/μl, based on the composition;

(b) at least one polar protic or polar aprotic solvent ("component (b)"), preferably having a cyclic molecule structure, in particular in an amount in the range of 0.5 to 40 vol %, in particular 1 to 35 vol %, especially 2 to 30 vol %, preferably 5 to 20 vol %, and particularly preferably 7 to 15 vol. %, based on the composition;

(c) at least one carboxylic acid amide and/or salts thereof ("component (c)"), in particular formamide and/or salts thereof, in particular in an amount in the range of 10 to 60 vol %, in particular 15 to 50 vol %, especially 17 to 40 vol %, and preferably 20 to 30 vol %, based on the composition;

(d) optionally at least one polysaccharide ("component (d)"), especially a neutral biopolysaccharide, and preferably dextran and/or the derivatives or salts thereof, in particular in an amount in the range of 0.1 to 50 wt %, in particular 1 to 40 wt %, especially 5 to 30 wt %, preferably 10 to 20 wt %, and particularly preferably 13 to 18 wt %, based on the composition;

(e) optionally at least one chemical buffer system ("component (e)"), in particular in the form of buffer salt(s), in particular in an amount in the range of 0.001 to 5 wt %, in particular 0.01 to 4 wt %, especially 0.1 to 3 wt %, preferably 0.5 to 2 wt %, and particularly preferably 1 to 1.5 wt %, based on the composition, and calculated as the sum of all components of the chemical buffer system;

(f) optionally, at least one blocking and/or stabilizing agent ("component (f)"), in particular in a concentration in the range of 0.001 μg/μl to 100 μg/μl, in particular 0.005 μg/μl to 80 μg/μl, especially 0.01 μg/μl to 40 μg/μl, preferably 0.05 μg/μl to 20 μg/μl, and particularly preferably 0.1 μg/μl to 10 μg/μl, based on the composition;

(g) optionally at least one inorganic salt ("component (g)"), in particular alkali salt and/or alkaline earth salt, preferably alkali chloride and/or alkaline earth chloride, and particularly preferably sodium chloride, in particular in an amount in the range of 0.01 to 15 wt %, in particular 0.05 to 10 wt %, especially 0.1 to 10 wt %, preferably 0.5 to 5 wt %, and particularly preferably 1 to 3 wt %, based on the composition; and (h) optionally at least one detergent and/or surfactant ("component (h)"), in particular in an amount in the range of 0.001 to 5 wt %, in particular 0.01 to 3 wt %, especially 0.05 to 2 wt %, preferably 0.1 to 1.5 wt %, and particularly preferably 0.12 to 1 wt %, based on the composition.

10. A composition, and in particular a composition for use in hybridization, in particular in situ hybridization, preferably automated in situ hybridization, in particular for the identification and/or for the detection of nucleic acids, preferably RNA and/or DNA, in a biological sample, preferably in one or more cells and/or in one or more nuclei, preferably a composition according to any one of the preceding embodiments, the composition comprising:

(a) at least one, preferably locus-specific, hybridization probe ("component (a)"), in particular in a concentration in the range of 0.1 ng/μl to 50 ng/μl, in particular 0.5 ng/μl to 50 ng/μl, especially 0.7 ng/μl to 8 ng/μl, and preferably 1 ng/μl to 5 ng/μl, based on the composition;

(b) at least one polar protic or polar aprotic solvent ("component (b)"), preferably having a cyclic molecule structure, preferably γ-butyrolactone, 2-pyrrolidone (γ-butyrolactam) and/or ethylene carbonate, in particular in an amount in the range of 0.5 to 40 vol %, in particular 1 to 35 vol %, especially 2 to 30 vol %, preferably 5 to 20 vol %, and particularly preferably 7 to 15 vol %, based on the composition;

(c) formamide and/or salts thereof ("component (c)"), in particular in an amount in the range of 10 to 60 vol %, in particular 15 to 50 vol %, especially 17 to 40 vol %, and preferably 20 to 30 vol %, based on the composition;

(d) optionally dextran and/or the derivatives or salts thereof ("component (d)"), in particular in an amount in the range of 0.1 to 50 wt %, in particular 1 to 40 wt %, especially 5 to 30 wt %, preferably 10 to 20 wt %, and particularly preferably 13 to 18 wt %, based on the composition;

(e) optionally at least one chemical buffer system, in particular in the form of buffer salt(s), preferably citrate and/or sodium chloride, ("component (e)"), in particular in an amount in the range of 0.001 to 5 wt %, in particular 0.01 to 4 wt %, especially 0.1 to 3 wt %, preferably 0.5 to 2 wt %, and particularly preferably 1 to 1.5 wt %, based on the composition, and calculated as the sum of all components of the chemical buffer system;

(f) optionally, at least one blocking and/or stabilizing agent ("component (f)"), in particular in a concentration in the range of 0.001 μg/μl to 100 μg/μl, in particular 0.005 μg/μl to 80 μg/μl, especially 0.01 μg/μl to 40 μg/μl, preferably 0.05 μg/μl to 20 μg/μl, and particularly preferably 0.1 μg/μl to 10 μg/μl, based on the composition;

(g) optionally at least one inorganic salt ("component (g)"), in particular alkali salt and/or alkaline earth salt, preferably alkali chloride and/or alkaline earth chloride, and particularly preferably sodium chloride, in particular in an amount in the range of 0.01 to 15 wt %, in particular 0.05 to 10 wt %, especially 0.1 to 10 wt %, preferably 0.5 to 5 wt %, and particularly preferably 1 to 3 wt %, based on the composition; and (h) optionally at least one polyalkylene glycol ether ("component (h)"), in particular in an amount in the range of 0.001 to 5 wt %, in particular 0.01 to 3 wt %, especially 0.05 to 2 wt %, preferably 0.1 to 1.5 wt %, and particularly preferably 0.12 to 1 wt %, based on the composition.

11. Use of a composition according to any one of the preceding embodiments with hybridization, in particular in situ hybridization, preferably automated in situ hybridization, in particular for the identification and/or for the detection of nucleic acids, preferably RNA and/or DNA, in a biological sample, preferably in one or more cells and/or in one or more nuclei.

12. A method for detecting nucleic acids, preferably RNA and/or DNA, and/or chromosomal aberrations in a biological sample, preferably in one or more cells and/or in one or more nuclei by way of hybridization, in particular in situ hybridization, and preferably automated in situ hybridization, using a composition according to any one of embodiments 1 to 10.

13. A method for detecting nucleic acids, preferably RNA and/or DNA, and/or chromosomal aberrations in a biological sample, preferably in one or more cells and/or in one or more nuclei by way of hybridization, in particular in situ hybridization, and preferably automated in situ hybridization, in particular the method according to embodiment 12, the method comprising the following steps:

(a) providing a biological sample, in particular based on one or more cells and/or one or more nuclei, preferably in the form of tissue, for in situ hybridization;

(b) providing a composition for use in the hybridization, wherein the composition comprises at least one, preferably locus-specific, hybridization probe ("component (a)"), at least one polar protic or polar aprotic solvent, preferably having a cyclic molecule structure, ("component (b)"), and at least one carboxylic acid amide and/or salts thereof, in particular formamide and/or salts thereof, in an amount greater than 10 vol %, based on the composition ("component (c)"), in particular a composition according to any one of embodiments 1 to 10;

(c) bringing the biological sample from method step (a) in contact with the composition from method step (b);

(d) denaturing the biological sample from method step (a) and the composition from method step (b), wherein the biological sample and the composition are denatured separately from one another, in particular prior to carrying out method step (c), or jointly, in particular after carrying out after method step (c);

(e) subsequently hybridizing the at least one, preferably locus-specific, hybridization probe comprised in the composition and the nucleic acids comprised in the biological samples; and (f) subsequently detecting the hybridized, preferably locus-specific, hybridization probes and/or the nucleic acids to be detected in the biological sample.

14. The method according to embodiment 13, wherein the method is carried out in an automated system and/or automatically; and/or wherein the composition in method step (c) is used in an amount in the range of 0.01 to 5,000 μl, in particular 0.1 to 2,500 μl, especially 1 to 1,500 μl, preferably 2 to 1,000 μl, particularly preferably 1 to 500 μl, most particularly preferably 20 to 250 μl, and still more preferably 40 to 150 μl; and/or

wherein method step (e) is carried out with movement, in particular a wave-like and/or continuous movement; and/or wherein method step (e) is carried out with short or with long hybridization durations and/or wherein method step (e) is carried out over a duration in the range of 10 min to 240 min, in particular in the range of 30 min to 180 min, especially in the range of 60 min to 150 min, and preferably in the range of 90 min to 130 min, or wherein method step (e) is carried out over a duration in the range of 1 h to 100 h, in particular 2 h to 80 h, especially 3 h to 50 h, preferably 4 h to 30 h, particularly preferably 5 h to 25 h, and still more preferably 8 h to 20 h.

15. A kit (kit of parts or system) for detecting nucleic acids, preferably RNA and/or DNA, and/or chromosomal aberrations in a biological sample, preferably in one or more cells and/or in one or more nuclei by way of hybridization, in particular in situ hybridization, and preferably automated in situ hybridization, wherein the kit includes a composition according to any one of embodiments 1 to 10 and/or wherein the kit is intended and/or used for carrying out a method according to any one of embodiments 12 to 14.

The invention claimed is:

1. In a composition for detecting nucleic acids and/or chromosomal aberrations in a biological sample via in situ hybridization, the composition comprising at least one fluorescent-labeled locus-specific hybridization probe ("component (a)") and water as a carrier or excipient, wherein the hybridization probe is selected from DNA, RNA, and locked nucleic acids (LNA), wherein the improvement comprises:

that the composition comprises:

2-pyrrolidone or 2-piperidone ("component (b)") in an amount of 2 to 13 vol % or wt %, based on the composition, and formamide and/or salts thereof ("component (c)") in an amount of 20 to 30 vol % based on the composition, wherein the composition comprises said component (b) and said component (c) in a volume-based ratio in the range of 1:10 to 1:3, said composition further comprising:

dextran sulfate ("component (d)"), and at least one inorganic salt ("component (g)") wherein the inorganic salt is sodium chloride.

2. The composition according to claim 1, wherein the composition comprises said dextran sulfate in an amount in the range of 10 to 20 wt %, based on the composition.

3. The composition according to claim 1, wherein the composition comprises said inorganic salt in an amount in the range of 0.5 to 5 wt %, based on the composition.

4. The composition according to claim 1, said composition further comprising at least one chemical buffer system ("component (e)").

5. The composition according to claim 4, where the at least one chemical buffer system is a citrate-based buffer system in an amount in the range of 0.1 to 3 wt %.

6. The composition of claim 5, wherein said citrate-based buffer system is an SSC (saline-sodium citrate) buffer system.

7. The composition according to claim 1, said composition further comprising at least one blocking and/or stabilizing agent ("component (f)") in an amount in the range of 0.1 µg/µl to 10 µg/µl.

8. The composition according to claim 1, further comprising at least one detergent and/or surfactant.

* * * * *